(12) United States Patent
Silverman et al.

(10) Patent No.: US 8,932,842 B2
(45) Date of Patent: *Jan. 13, 2015

(54) AMINOPYRIDINE DIMER COMPOUNDS, COMPOSITIONS AND RELATED METHODS FOR NEURONAL NITRIC OXIDE SYNTHASE INHIBITION

(71) Applicant: Northwestern University, Evanston, IL (US)

(72) Inventors: Richard B. Silverman, Northbrook, IL (US); Fengtian Xue, Baton Rouge, LA (US); He Huang, Chicago, IL (US)

(73) Assignee: Northwestern University, Evanston, IL (US)

( * ) Notice: Subject to any disclaimer, the term of this patent is extended or adjusted under 35 U.S.C. 154(b) by 172 days.

This patent is subject to a terminal disclaimer.

(21) Appl. No.: 13/573,654

(22) Filed: Oct. 1, 2012

(65) Prior Publication Data

US 2013/0040359 A1 Feb. 14, 2013

Related U.S. Application Data

(63) Continuation-in-part of application No. 12/704,205, filed on Feb. 11, 2010, now Pat. No. 8,278,084.

(60) Provisional application No. 61/207,362, filed on Feb. 11, 2009.

(51) Int. Cl.
*C07D 401/12* (2006.01)
*C07D 401/10* (2006.01)
*C07D 401/14* (2006.01)
*C12N 9/99* (2006.01)
*C12N 9/02* (2006.01)

(52) U.S. Cl.
CPC ............ *C07D 401/10* (2013.01); *C07D 401/14* (2013.01); *C07D 401/12* (2013.01); *C12N 9/0075* (2013.01); *C12Y 114/13039* (2013.01)
USPC ............ 435/184; 544/364; 546/256; 546/264

(58) Field of Classification Search
CPC ...................... C12N 9/0075; C12Y 114/13039
USPC ................................... 435/184; 546/256, 264
See application file for complete search history.

(56) References Cited

U.S. PATENT DOCUMENTS

| | | | |
|---|---|---|---|
| 6,894,069 B2 | 5/2005 | Peetres et al. | |
| 7,470,790 B2 | 12/2008 | Silverman | |
| 8,278,084 B2 * | 10/2012 | Silverman et al. | ............ 435/184 |
| 2008/0108814 A1 | 5/2008 | Silverman et al. | |

FOREIGN PATENT DOCUMENTS

| | | |
|---|---|---|
| WO | WO96-11910 | 4/1996 |
| WO | WO00-33844 | 6/2000 |
| WO | WO01-74779 | 10/2001 |
| WO | WO2005-100349 | 10/2005 |
| WO | WO2006-021454 | 3/2006 |

OTHER PUBLICATIONS

Chemical Communications (Cambridge), (1998), vol. 12, p. 1313-1314 by Bielawski et al.

* cited by examiner

*Primary Examiner* — Yong Chu
(74) *Attorney, Agent, or Firm* — Reinhart Boerner Van Deuren s.c.

(57) ABSTRACT

Nitric oxide synthase (NOS) inhibitor compounds comprising bi-terminal aromatic ring moieties, and related methods of NOS inhibition.

20 Claims, 5 Drawing Sheets

3

AMINOPYRIDINE DIMER COMPOUNDS, COMPOSITIONS AND RELATED METHODS FOR NEURONAL NITRIC OXIDE SYNTHASE INHIBITION

This application is a continuation-in-part of and claims priority benefit from application Ser. No. 12/704,205 filed Feb. 11, 2010 and issued as U.S. Pat. No. 8,278,084 on Oct. 2, 2012 and provisional application Ser. No. 61/207,362 filed Feb. 11, 2009, each of which is incorporated herein by reference in its entirety.

This invention was made with government support under grant number R01 GM049725 awarded by the National Institutes of Health. The government has certain rights in the invention.

BACKGROUND OF THE INVENTION

The neuronal isozyme of nitric oxide synthase (nNOS) catalyzes the oxidation of L-arginine to L-citrulline in the brain, generating small molecule nitric oxide (NO), a critical biological signaling molecule for neurotransmission. Significant research has shown that the overexpression of nNOS is implicated in various neurological diseases, including Parkinson's, Alzheimer's, Huntington's diseases, and neuronal damage due to stroke. Thus, selective inhibition of nNOS over its closely related isoforms, endothelial NOS (eNOS) and inducible NOS (iNOS), can provide a promising strategy in developing therapeutics for the treatment of neurodegenerative diseases.

A significant amount of research has been devoted to the development of nNOS selective inhibitors. Chiral pyrrolidine-based inhibitors (1 and 2, FIG. 1) have excellent potency ($K_i$=85 and 15 nM, respectively) and high selectivity for nNOS over eNOS (1000- and 2100-fold, respectively) and iNOS (110- and 630-fold, respectively). However, results from animal studies indicate that these inhibitors do not optimally penetrate the blood brain barrier (BBB), and such results tend to impede application of the compounds as candidates for treatment of neurodegenerative diseases. It was reasoned that the multiple nitrogen atoms on compounds 1 and 2 were positively charged at physiological pH, which decreased penetration across the BBB by passive diffusion. Moreover, the syntheses of 1 and 2 are complicated and somewhat impractical for large scale preparation and structure-activity relationship optimization.

SUMMARY OF THE INVENTION

In light of the foregoing, it is an object of the present invention to provide compounds and related methods of use for the selective inhibition of neuronal nitric oxide synthase, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide one or more small molecule and/or non-peptide compounds exhibiting selective nNOS inhibition, over other enzyme isoforms and providing improved membrane permeability and bioavailability.

It can be an object of the present invention to provide one or more with such non-peptide compounds for in vitro use and study under conditions promoting nitric oxide production, such conditions indicative of one or more mammalian disease states.

It can be an object of the present invention, alone or in conjunction with one or more of the preceding objectives, to provide one or more such compounds or corresponding pharmaceutical compositions enabling in vivo treatment of such mammalian disease states, such compounds as can be used to enhance penetration through biomembranes—in particular, the blood brain barrier—and/or to increase the bioavailability of such compounds.

Other objects, features, benefits and advantages of the present invention will be apparent from this summary and the following descriptions of certain embodiments of such compounds compositions and/or methods, and will be readily apparent to those skilled in the art enzyme activity and inhibition and having knowledge of the synthetic techniques described therewith. Such objects, features, benefits and advantages will be apparent from the above as taken into conjunction with the accompanying examples, data, figures and references incorporated herein, together with all reasonable inferences to be drawn therefrom.

In part, the present invention can be directed to compounds of a formula

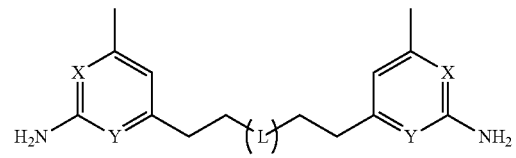

wherein L can comprise a divalent hydrophobic and/or lipophilic linker moiety; and each X and each Y is independently selected from CH and N, providing one of X and Y in each terminal ring moiety is N. As would be understood by those skilled in the art made aware of this invention, such hydrophobicity and/or lipophilicity can be considered and determined in the context of net molecular positive charge, such charge as compared to and less than the positive charge of pyrrolidine-based inhibitor compounds of the prior art. Such a compound can be present as a salt, hydrate and/or solvate thereof and, optionally, in a pharmaceutical composition comprising such a compound and a pharmaceutically-acceptable carrier.

The structure of such a compound is limited only by a choice of starting material or reagent, in accordance with synthetic procedures of the sort described herein. Likewise, if comprising one or more chiral centers, the present compounds are without stereochemical limitation. Such compounds and/or their intermediates are available as racemic mixtures from which isomers can be resolved or are diastereomers, from which cis and/or trans isomers can be separated. As mentioned above, it will be understood by those skilled in the art that compounds of this invention can comprise an acid salt (e.g., an ammonium salt) of any such compound. Without limitation, certain embodiments can be partially or fully protonated, and the counter ion(s) can be a conjugate base of a protic acid.

In part, this invention can be directed to compounds of a formula

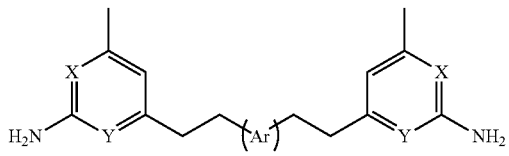

wherein X and Y can be as described above and Ar can be selected from divalent aryl moieties, including but not limited to fused-aromatic ring moieties and aryl moieties (whether or not fused-ring) comprising one or more heteroatom ring substitutions, together with salts (e.g., ammonium salts), hydrates and/or solvates of such compounds. Without limitation, in certain embodiments, whether or not substituted, Ar can be selected from divalent naphthyl, phenyl and pyridinyl moieties. Regardless, terminal ring (e.g., aminopyridine) pendency therefrom can vary. Such pendency can be either symmetrical or unsymmetrical with respect to a particular aryl moiety. Regardless, as discussed above, such compounds are not restricted by either charge or medium, and can be provided in the context of a pharmaceutical composition comprising such a compound and, optionally, a pharmaceutically-acceptable carrier.

In part, the present invention can also be directed to a neuronal nitric oxide synthase inhibitor compound of a formula

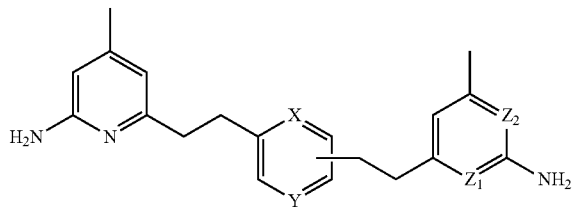

wherein X and Y can be independently selected from CH and N, providing at least one of X and Y is CH; and $Z_1$ and $Z_2$ can be independently selected from CH and N, providing one of $Z_1$ and $Z_2$ is N. As discussed above, such compounds are not restricted by charge or medium, and can be present as a salt, hydrate and/or solvate thereof whether or not part of pharmaceutical composition. In certain non-limiting embodiments, Y can be N. In certain such embodiments, $Z_1$ can be N and $Z_2$ can be CH. Certain such compounds can have symmetrical pendency with respect to the pyridinyl moiety (e.g., without limitation, Y can be N with 3,5-bis-substitution—meta-linkage or coupling—of the pendent aminopyridine moieties thereto).

More generally, as demonstrated below, the structure of such a compound is limited only by choice of starting material or reagent, enroute to amino-substituted aromatic terminal ring (e.g., aminopyridine) components or substructures, such substructures as are discussed more fully below and/or in co-pending application Ser. No. 11/906,283 and U.S. Pat. No. 7,470,790, each of which is incorporated herein by reference in its entirety. Accordingly, various compounds of this invention can, optionally, comprise various other terminal aromatic or heteroaromatic ring substructures or substituents thereof, such as but not limited to the substructures, moieties and/or groups described in the aforementioned incorporated references (e.g., substructure I, therein, and substituent $R_1$ thereof). Regardless, the terminal ring and linker moieties of such compounds are limited only by dimension and structure, as can be considered in the context of intramolecular distance between such bi-terminal rings and position thereof in the binding sites of an nNOS enzyme. Such considerations are illustrated and discussed more fully, below. Without limitation, in certain such embodiments, such a compound can comprise a divalent aryl or heteroaryl linker moiety, such moieties as are available through synthetic techniques of the sort described below and limited only by choice of starting material or reagent.

In part, the present invention can also be directed to a neuronal nitric oxide synthase inhibitor compound of a formula

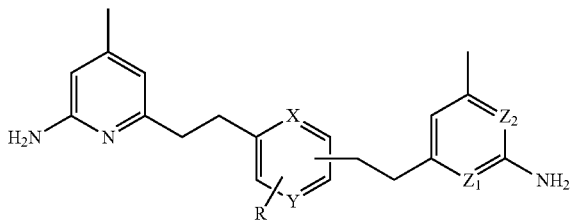

wherein R can be selected from H, halogen, amino, nitrile, alkyl, haloalkyl, aminoalkyl, cyanoalkyl, cycloalkyl and azacycloalkyl moieties; X and Y can be independently selected from CR' and N, where R' can be selected from H and R, providing at least one of X and Y is CR'; and $Z_1$ and $Z_2$ can be independently selected from CH and N, providing one of $Z_1$ and $Z_2$ is N. As discussed above, such compounds are not restricted by charge or medium, and can be present as a salt, hydrate and/or solvate thereof whether or not part of pharmaceutical composition. In certain non-limiting embodiments, both X and Y can be CR'. In certain such embodiments X can be CH and Y can be CR. Certain such compounds can have a symmetrical pendency (e.g., without limitation, each aminopyridine moiety can have an ortho- or meta-relationship with respect to CR. In certain other non-limiting embodiments, Y can be N. In certain such embodiments, $Z_1$ can be N and $Z_2$ can be CH. Certain such compounds can have symmetrical pendency with respect to the pyridinyl moiety (e.g., without limitation, Y can be N with 3,5-bis-substitution—meta-linkage or coupling—of the pendent aminopyridine moieties thereto).

In part, the present invention can also be directed to a neuronal nitric oxide synthase inhibitor compound of a formula

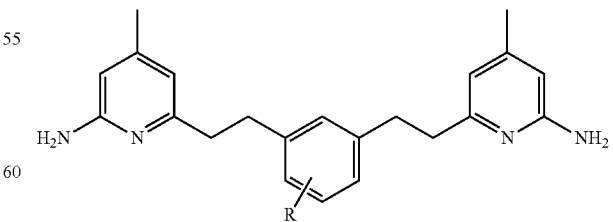

wherein R can be selected from H, halogen, amino, nitrile, alkyl, haloalkyl, aminoalkyl, cyanoalkyl, cycloalkyl and azacycloalkyl moieties. As discussed above, such compounds are not restricted by charge or medium, and can be present as a salt, hydrate and/or solvate thereof whether or not part of pharmaceutical composition. In certain non-limiting embodiments, R can be selected from nitrile and aminoalkyl moieties. Certain such compounds can have symmetrical pendency with respect to such an R moiety. Without limitation, each such pendent aminopyridine moiety can have a meta-relationship to R.

In part, the present invention can also provide a method of inhibiting neuronal nitric oxide synthase. Such a method can comprise contacting, whether in vitro or in vivo, a neuronal nitric oxide synthase with an effective amount of any one or more of the present compounds or compositions, including but not limited to those illustrated by the following examples, figures, accompanying synthetic schemes and/or incorporated references. More specifically, as also supported herein, the present invention can provide a method for selective inhibition of neuronal nitric oxide synthase. Regardless, such methods can comprise providing a compound or corresponding pharmaceutical composition of this invention; and contacting a nitric oxide synthase with such a compound/composition. In certain embodiments, as demonstrated below, such contact or administration to a mammalian subject can selectively inhibit neuronal nitric oxide synthase over inducible and endothelial isoforms.

DETAILED DESCRIPTION OF CERTAIN EMBODIMENTS

Figure 1:
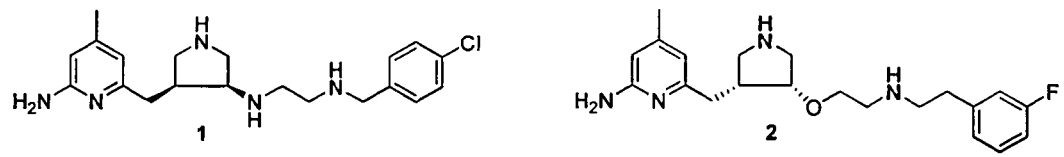
FIG. 1. Structures of prior art compounds 1 and 2.
Figure 2A:
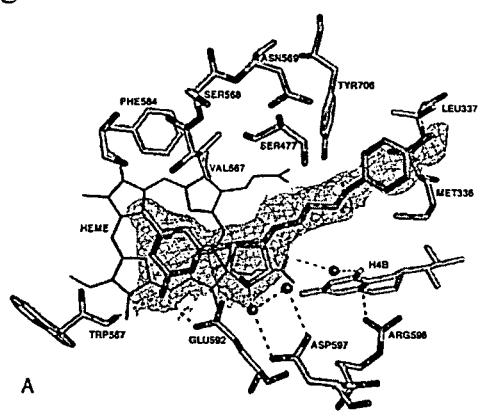
FIGS. 2A-B. (A) Crystal structure of nNOS with prior art compound 1 in the active site; (B) crystal structure of nNOS with prior art compound 2 in the active site.
Figure 2B:
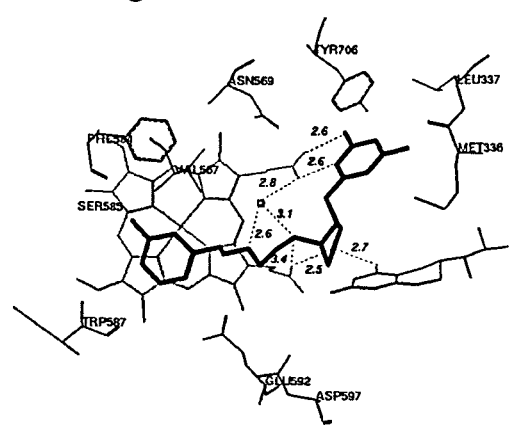

Crystal structures of nNOS with both prior art inhibitors 1 and 2 have been solved. As shown in FIG. 2A, the aminopyridine moiety of 1 binds to the heme, with the p-chloro-benzyl tail extending to a peripheral pocket (Tyr$^{706}$, Leu$^{336}$, and Met$^{337}$) at the edge of the substrate binding channel. On the other hand, inhibitor 2 binds to nNOS employing a "reverse" mode (FIG. 2B): the aminopyridine binds to the peripheral pocket (Tyr$^{706}$, Leu$^{336}$, and Met$^{337}$), while the m-fluorophenyl moiety of 2 is positioned above the aromatic system of the heme. That the aminopyridine moiety can occupy two different binding sites in nNOS provided a new strategy to design certain nNOS inhibitor compounds of this invention.

Figure 3:
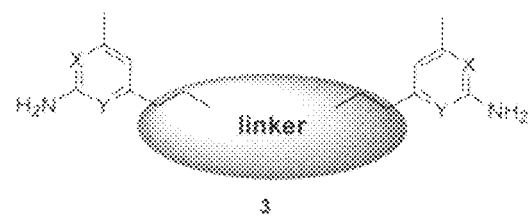
FIG. 3. General structure of inhibitor 3, in accordance with this invention.

Based on the crystal structure data of inhibitors 1 and 2, a new class of inhibitors (3) was designed with two aminopyridine moieties pendent to and coupled by an optimizable linker moiety (FIG. 3). It was hypothesized that a potent and selective nNOS inhibitor can be achieved by optimizing the length and structure of the linker. Compared to the "parent compounds" (1 and 2), this new class of compounds demonstrates several intriguing advantages. First, since the secondary amine groups of 1 and 2 are replaced by a hydrophobic linker, inhibitor 3 should demonstrate increased lipophilicity, which could improve bioavailability of the inhibitors. Second, 3 can be synthesized by a short synthetic route. The structural simplicity of 3 can significantly increase the efficiency of the synthesis. Finally, the modular design of 3 lends itself to structure-activity optimization.

Inhibitors 3a-d, a group of compounds employing a divalent, bis-substituted naphthyl linker, were first synthesized and tested against NOSs because the lengths of these inhibitors are similar to the lengths of prior art compounds 1 and 2. The details of the syntheses are outlined in Schemes 1-2.

As shown in Scheme 1, 3a was synthesized using a two-step procedure. First, N-Boc-2-amino-4,6-dimethylpyridine (4), prepared by Boc-protection of the commercially-available aminopyridine, was treated with NaH, and the resulting anion was allowed to react with bis-bromide 5a to give 6a in good yields. Next, the two Boc-protecting groups of 6a were removed with TFA to generate 3a in high yields.

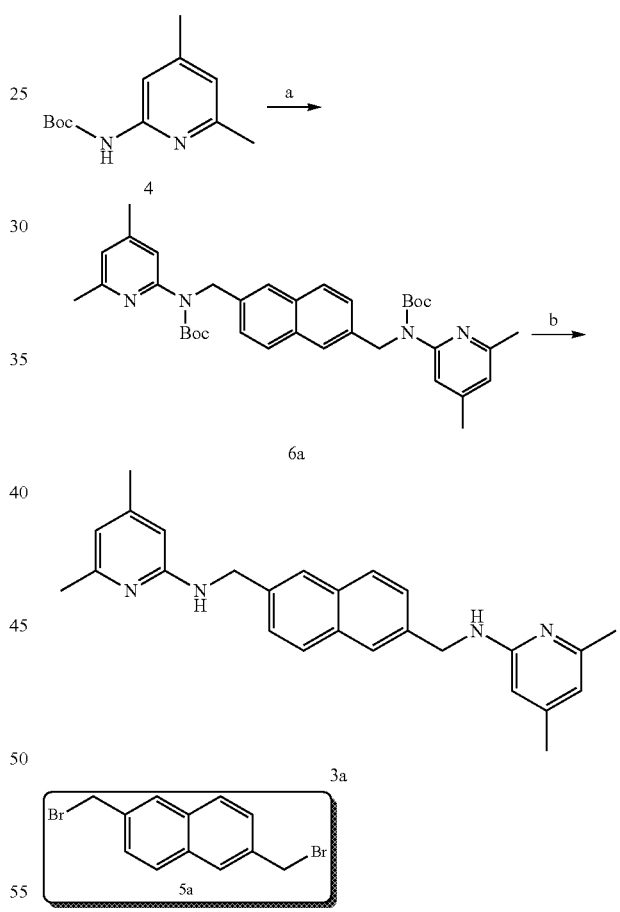

Scheme 1. Synthesis of 3a.$^{a}$ $^{a}$ Reagents and conditions:
(a) (i) NaH, 0° C., 15 min, (ii) 5a, 6h, 81%;
(b) TFA/CH$_2$Cl$_2$ (1:1), r.t., 8h, 90%.

The synthesis of 3b began with 2,5-dimethylpyrrole-protected 2-amino-4,6-dimethylpyridine (7). Compound 7 was treated with n-BuLi at −78° C., and the resulting anion was allowed to react with 5a or 5b to give 6b-d. Next, the 2,5-dimethylpyrrole protecting groups were removed with hydroxylamine hydrochloride at 100° C. to generate 3b-d in excellent yields.

Scheme 2. Synthesis of 3b-d.

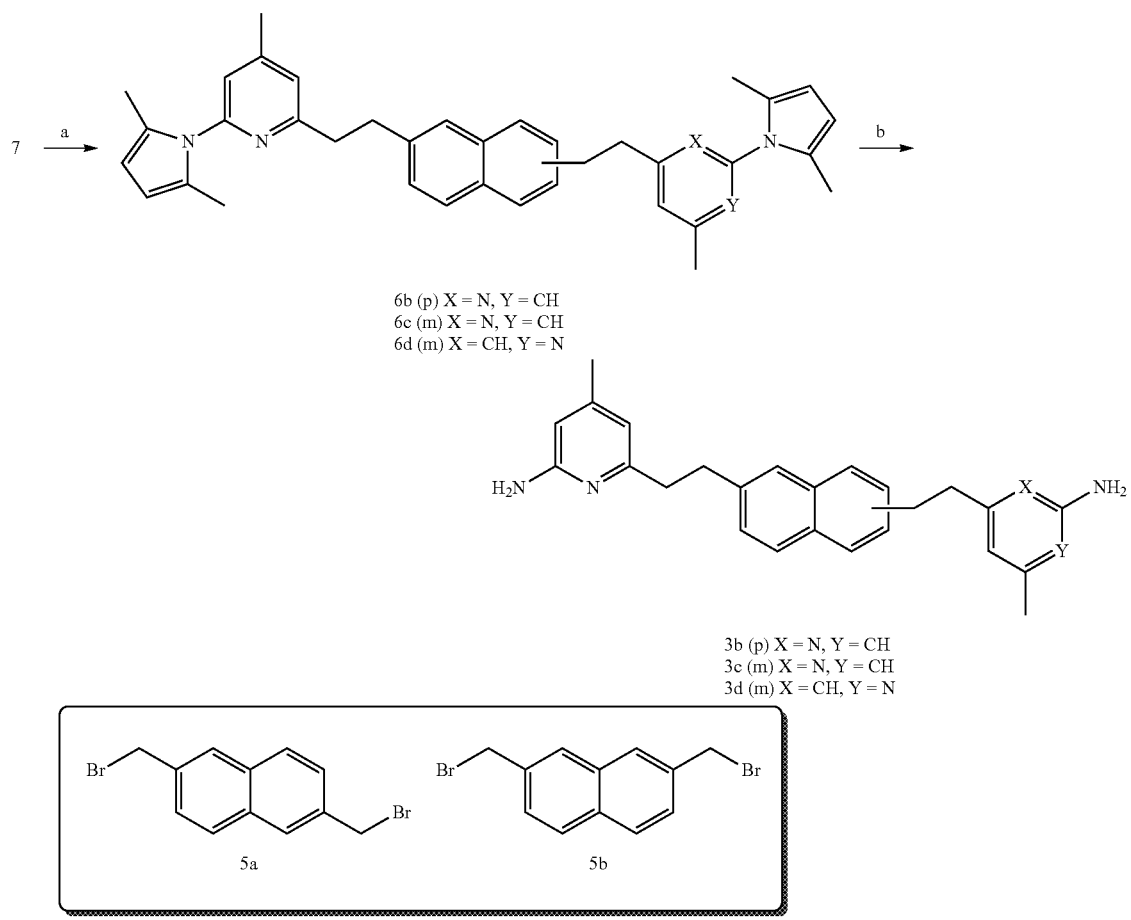

<sup>a</sup>Reagents and conditions: (a) (i) n-BuLi, -78° C. - 0° C., 30 min, (ii) 5a or 5b, 55%; (b) NH$_2$OH•HCl, EtOH/H$_2$O (2:1), 100° C., 20 h, 90%.

The activities of 3a-d were determined against three different isoforms of NOS including rat nNOS, bovine eNOS, and murine iNOS;[21] the $K_i$ values were calculated and are listed in Table 1. Inhibitor 3a (Table 1, entry 1), an internal amidine dimer, showed poor activity against nNOS, whereas 3b (Table 1, entry 2), which has a structure similar to 3a except for the external amidine functionalities, showed good potency for nNOS ($K_i$=241 nM) and some selectivity for nNOS over eNOS (7-fold) and iNOS (9-fold). A direct comparison of 3a and 3b indicated that the external amidine functional group is the key factor for tight binding. Inhibitor 3c (Table 1, entry 3), a regioisomer of 3b, showed very good potency ($K_i$=102 nM). However, an unsymmetrical regioisomer of 3c, inhibitor 3d (Table 1, entry 4) showed little activity for nNOS. A comparison between 3d and 3c shows that the orientation of the aminopyridine fragment can have an affect on binding.

TABLE 1

$K_i{}^a$ values and selectivity of 3a-d.

| Entry | cmpd | nNOS (nM) | eNOS (nM) | iNOS (nM) | n/e[b] | n/i[b] |
|---|---|---|---|---|---|---|
| 1 | 3a | >11500 | N.D.[c] | N.D.[c] | N.D.[c] | N.D.[c] |
| 2 | 3b | 241 | 1740 | 2270 | 7.22 | 9.42 |
| 3 | 3c | 102 | 1520 | 2050 | 14.9 | 20.1 |
| 4 | 3d | >500 | N.D.[c] | N.D.[c] | N.D.[c] | N.D.[c] |

[a]The $K_i$ values were calculated based on the directly measured IC$_{50}$ values, which represent at least duplicate measurements with standard deviations of ±10%.
[b]The ratio of $K_i$ (eNOS or iNOS) to $K_i$ (nNOS).
[c]Data has not been determined.

Next, aminopyridine dimers 3e-3i, employing either a 1,3-bis or a 1,4-bis-substituted phenyl group as linkers, were synthesized using an analogous procedure to that for 3b-d (Schemes 3-4). The syntheses of inhibitors 3e-h are shown in Scheme 3. Compound 7 was treated with n-BuLi at −78° C., and the resulting anion was allowed to react with 5c or 5d to give 6e-h. The 2,5-dimethylpyrrole protecting groups of 6e-h were removed with hydroxylamine hydrochloride at 100° C. to generate 3e-h in excellent yields.

Scheme 3. Synthesis of 3e-h.

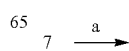

-continued

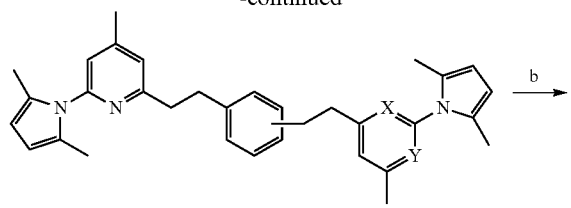

6e (p) X = N, Y = CH
6f (p) X = CH, Y = N
6g (m) X = N, Y = CH
6h (m) X = CH, Y = N

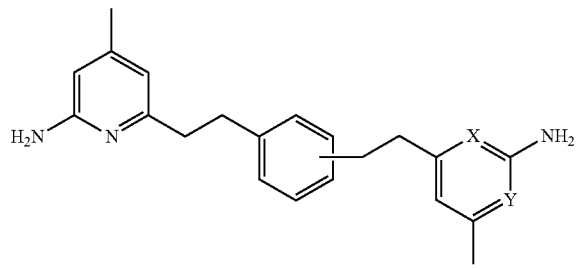

3e (p) X = N, Y = CH
3f (p) X = CH, Y = N
3g (m) X = N, Y = CH
3h (m) X = CH, Y = N

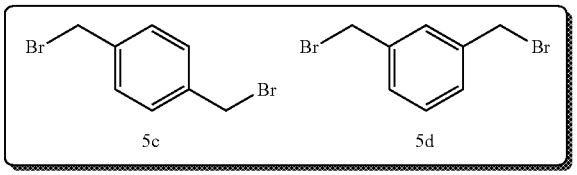

5c   5d

[a]Reagents and conditions: (a) (i) n-BuLi, -78° C. - 0° C., 30 min, (ii) 5c or 5d; (b) NH$_2$OH•HCl, EtOH/H$_2$O (2:1), 100° C., 20 h, 85-90%.

Scheme 4 shows the synthesis of 3i, which is similar to that for 3e-h except 7 was treated with LDA at 0° C.

Scheme 4. Synthesis of 3i.

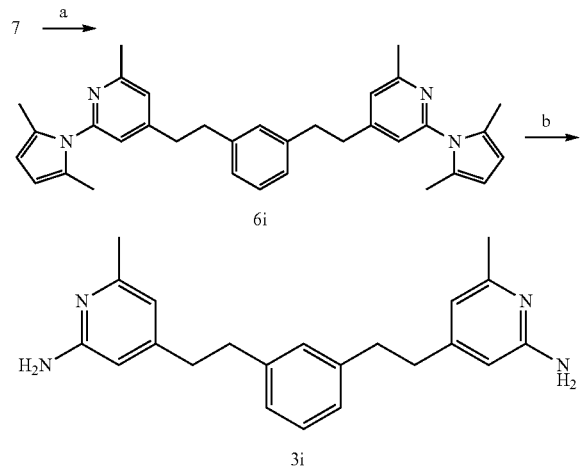

[a]Reagents and conditions: (a) (i) LDA, 0° C., 30 min, (ii) 5d, 65%; (b) NH$_2$OH•HCl, EtOH/H$_2$O (2:1), 100° C., 20 h, 88%.

1,4-Bis-substituted inhibitor 3e (Table 2, entry 1) showed improved potency (97 nM) and selectivity for nNOS over eNOS (25-fold) and iNOS (25-fold) than 3a-d which have naphthyl linkers. However, unsymmetrical regioisomer 3f was inactive (Table 2, entry 2). Interestingly, 1,3-bis-substituted inhibitors 3g and 3h (Table 2, entries 3 and 4) showed excellent potency (49 and 38 nM, respectively) for nNOS. Moreover, 3h showed good selectivity for nNOS over eNOS (111-fold) and iNOS (71.8-fold). Symmetric compound 3i (Table 2, entry 5) was also synthesized, with both amidine groups pointing away from the linker. Compound 3i showed poor activity for nNOS. This result again suggests that the orientation of the amidine functionality can have an affect on tight binding.

TABLE 2

$K_i{}^a$ values and selectivity of 3e-i.

| Entry | cmpd | nNOS (nM) | eNOS (nM) | iNOS (nM) | n/e[b] | n/i[b] |
|---|---|---|---|---|---|---|
| 1 | 3e | 97 | 2390 | 2410 | 24.6 | 24.8 |
| 2 | 3f | 167 | N.D.[c] | N.D.[c] | N.D.[c] | N.D.[c] |
| 3 | 3g | 49 | 1410 | 682 | 28.8 | 13.9 |
| 4 | 3h | 38 | 4200 | 2730 | 111 | 71.8 |
| 5 | 3i | 2250 | N.D.[c] | N.D.[c] | N.D.[c] | N.D.[c] |

[a]The $K_i$ values were calculated based on the directly measured IC$_{50}$ values, which represent at least duplicate measurements with standard deviations of ±10%.
[b]The ratio of $K_i$ (eNOS or iNOS) to $K_i$ (nNOS).
[c]Data has not been determined.

To further improve the potency and selectivity, the 1,3-bis-substituted phenyl linker was modified. As shown in Scheme 5, inhibitors 3j-m, with 3,5-bis-substituted pyridine or 2,6-bis-substituted pyridine as the linker, were synthesized. First, 7 was treated with n-BuLi at −78° C., and the resulting anion was allowed to react with 5e or 5f to give 6j-m. The 2,5-dimethylpyrrole protecting groups of 6j-m were removed with hydroxylamine hydrochloride at 100° C. to generate 3j-m in very good yields.

Scheme 5. Synthesis of 3j-m.

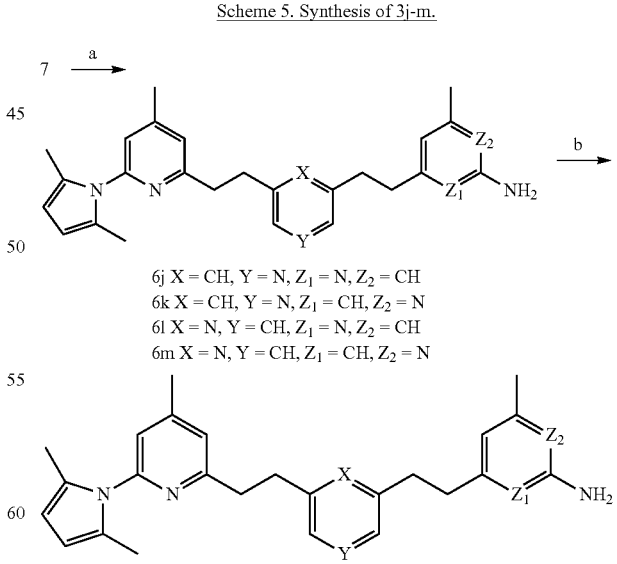

6j X = CH, Y = N, Z$_1$ = N, Z$_2$ = CH
6k X = CH, Y = N, Z$_1$ = CH, Z$_2$ = N
6l X = N, Y = CH, Z$_1$ = N, Z$_2$ = CH
6m X = N, Y = CH, Z$_1$ = CH, Z$_2$ = N

3j X = CH, Y = N, Z$_1$ = N, Z$_2$ = CH
3k X = CH, Y = N, Z$_1$ = CH, Z$_2$ = N
3l X = N, Y = CH, Z$_1$ = N, Z$_2$ = CH
3m X = N, Y = CH, Z$_1$ = CH, Z$_2$ = N

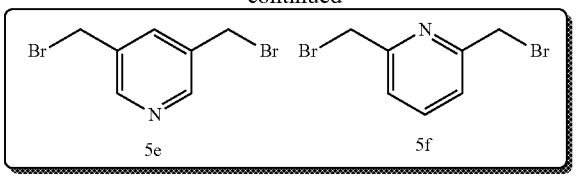

*Reagents and conditions: (a) (i) n-BuLi, -78° C. - 0° C., 30 min, (ii) 5e or 5f; (b) NH₂OH•HCl, EtOH/H₂O (2:1), 100° C., 20 h, 80-85%.

TABLE 3

$K_i{}^a$ values and selectivity of 3j-3m.

| Entry | cmpd | nNOS (nM) | eNOS (nM) | iNOS (nM) | n/e[b] | n/i[b] |
|---|---|---|---|---|---|---|
| 1 | 3j | 28 | 2680 | 1450 | 96 | 52 |
| 2 | 3k | 103 | 16100 | 1910 | 156 | 19 |

[a]The $K_i$ values were calculated based on the directly measured $IC_{50}$ values, which represent at least duplicate measurements with standard deviations of ±10%.
[b]The ratio of $K_i$ (eNOS or iNOS) to $K_i$ (nNOS).

Inhibitor 3j showed excellent potency ($K_i$=28 nM) and good selectivity for nNOS over eNOS (96-fold) and iNOS (52-fold) (Table 3, entry 1). Even though inhibitor 3k showed a small drop in potency ($K_i$=103 nM), it exhibited improved selectivity for nNOS over eNOS (156-fold).

Figure 4:
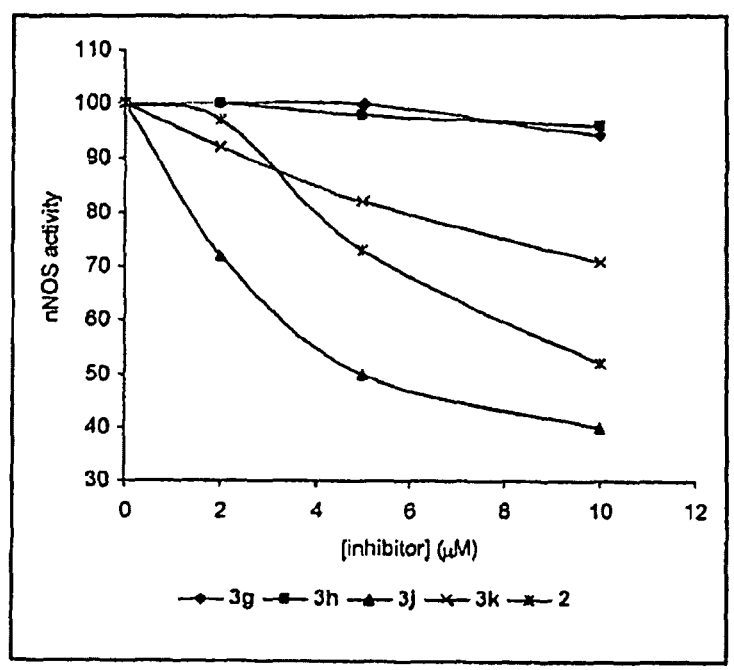
FIG. 4. Inhibition of nNOS in 293T cells overexpressing nNOS (293T/nNOS cells). 293T/nNOS cells were treated with A23187 (5 μM) and various concentrations of inhibitors 2 and 3g-3k. After eight hours, the amount of nitrite in culture media was quantified with the Griess reagent. Each data point is an average of two independent experiments.

The activities of compounds, 3g, 3h, 3j, and 3k, were further tested in a cell-based assay. As shown in FIG. 4, inhibitors 3g and 3h, with a phenyl group as the linker, showed almost no activity in the cell-based assay, suggesting that these compounds are blocked by the cellular membrane. Inhibitors 3j and 3k, however, showed very good membrane penetration ability. Most interestingly, compound 3j has an $IC_{50}$ value of 5 μM, which is more than two-fold better than parent compound 2. These results suggest again that the aminopyridine dimer (3) is a strong candidate for future development of bioavailable nNOS inhibitors.

To further evaluate potency and selectivity, and illustrating use of substituted aryl linker components in various other embodiments of this invention, a representative substituted linker moiety was prepared as shown below in Scheme 6. Amine substituted isophthalate 8 was protected with acetonylacetone. Bromination of homologous alcohol 10 provided bis(bromomethyl) linker compound 5g. As shown below, and with reference to the following examples, various other substituted linker compounds, whether or not amino substituted, can be prepared from the corresponding starting materials, using analogous synthetic techniques or straight forward variations thereof as would be understood by those skilled in the art. Regardless, with reference to several of the preceding synthetic schemes and as shown in Scheme 7, pyrrole-protected aminopyridine compound 7 was reacted with linker compound 5g to give intermediate 6n. The pyrrole protecting groups were removed to generate inhibitor 3n, in good yield.

Scheme 6. Synthesis of pyrrole-protected bis-bromide linker 5g.

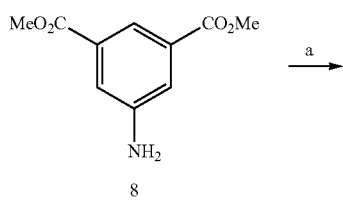

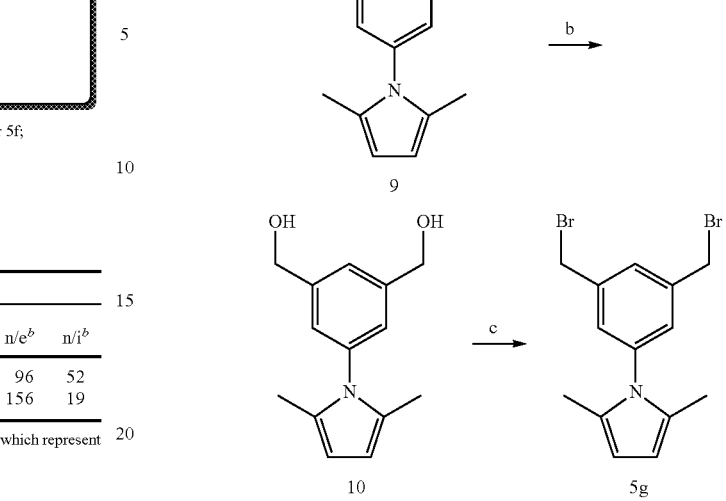

*Reagents and conditions: (a) acetonylacetone, p-TsOH, toluene, reflux, 12 h, 92%; (b) Dibal-H, THF, -78° C. to r.t., 6 h, 97%; (c) Ph₃P, CBr₄, dichloromethane (DCM), r.t., 1 h, 79%.

Scheme 7. Synthesis of amino-substituted inhibitor 3n.

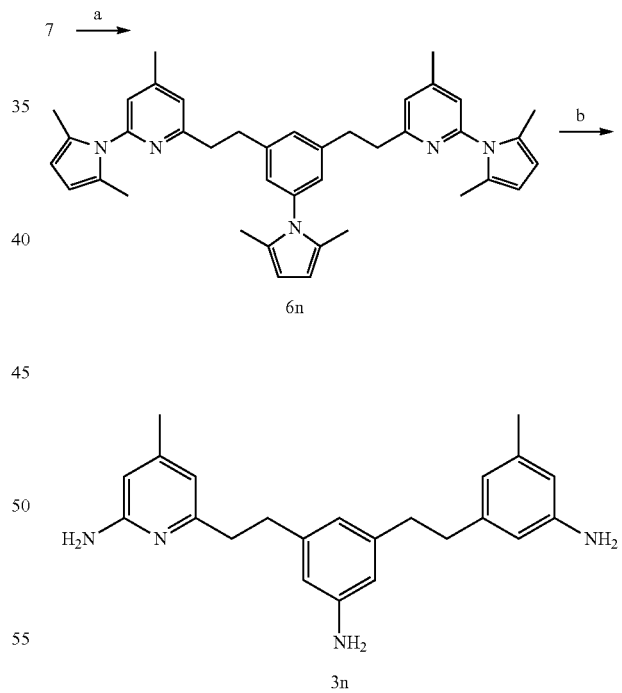

*Reagents and conditions: (a) (i) n-BuLi, -78° C. - 0° C., 30 min, (ii) 5g, 55%; (b) NH₂OH•HCl, EtOH/H₂O (2:1), 100° C., 36 h, 85%.

As a continuation of this study, and to demonstrate incorporation of substituted linker moieties of the sort discussed above, various other aminopyridine dimer compounds were prepared and evaluated. With reference to Scheme 8, a synthetic route for compounds such as HH025, HH027, HH026, and HH032 (FIG. 5) is described below.

Scheme 8.
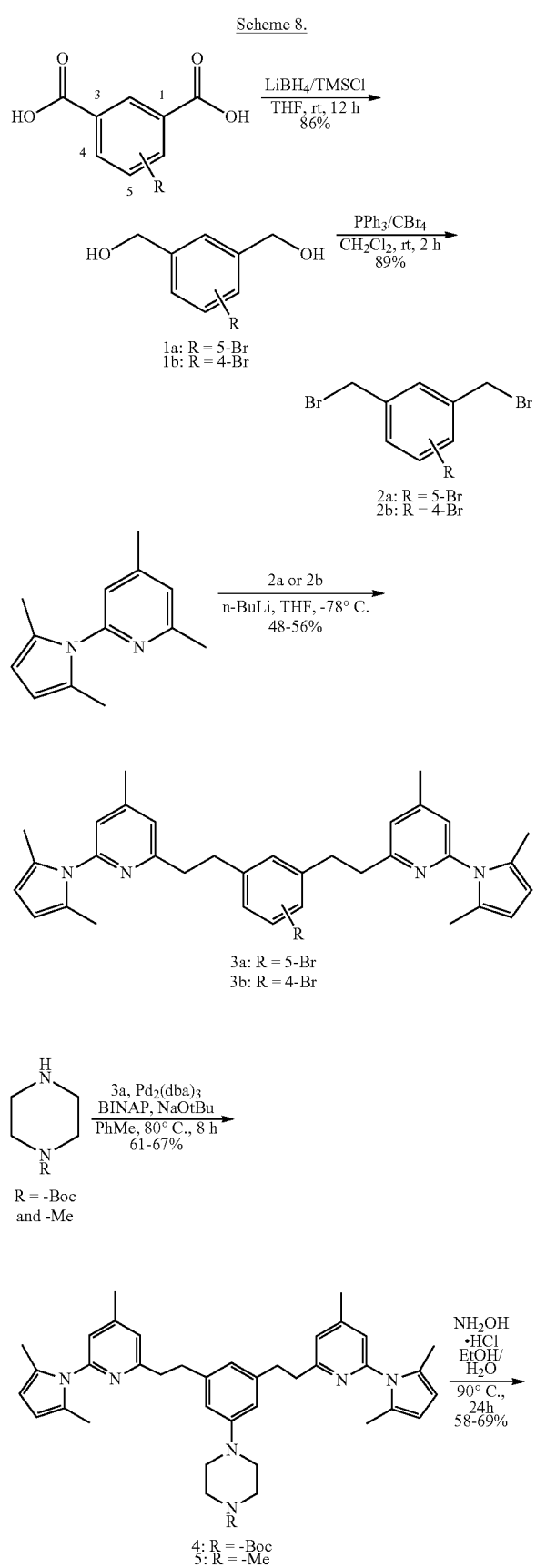
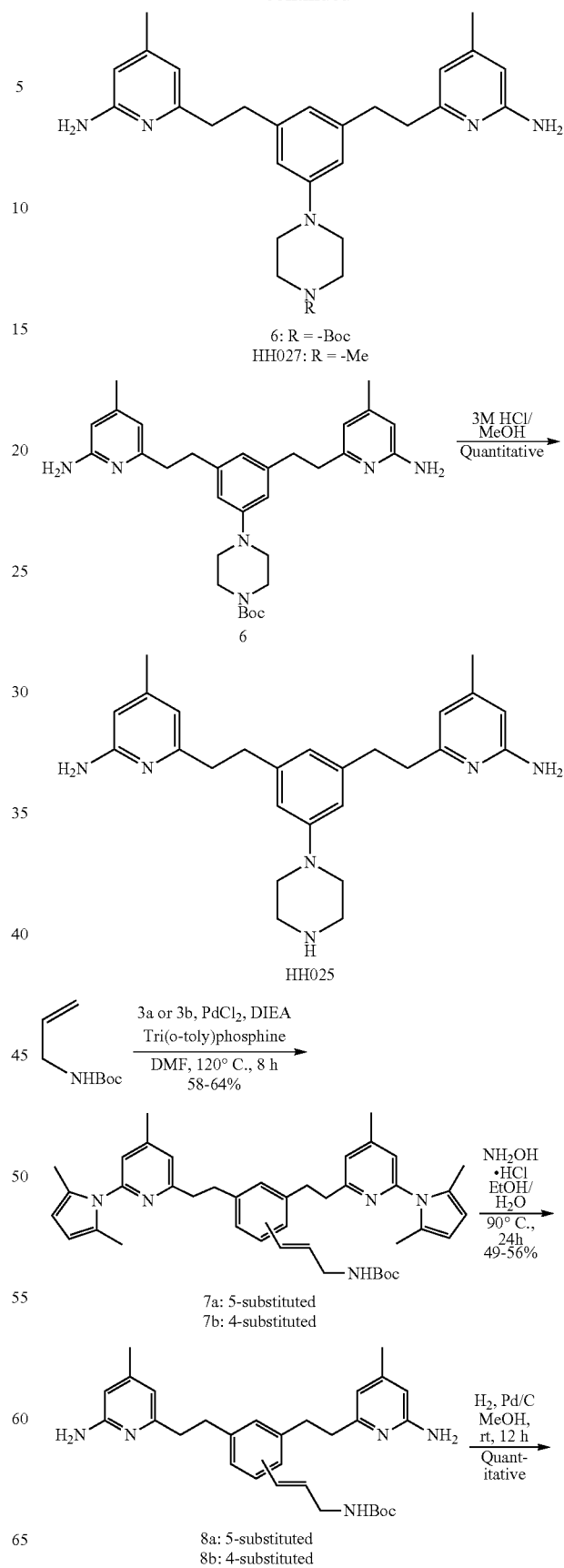

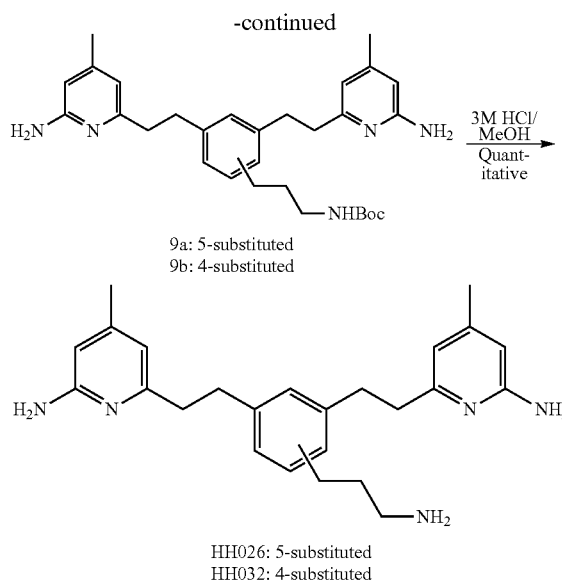

9a: 5-substituted
9b: 4-substituted

HH026: 5-substituted
HH032: 4-substituted

The carboxyl groups of bromo-substituted sophthalic acids were reduced to corresponding alcohol groups in good yields, followed by bromination to generate bis(bromomethyl) intermediates 2a and 2b. 2-(2,5-Dimethyl-1H-pyrrol-1-yl)-4,6-dimethylpyridine was treated with n-butyllithium, then reacted with 2a or 2b. Subsequent palladium-catalyzed amination of 3a with N-monosubstituted piperazines gave the corresponding aromatic amines. Deprotection of 4 and 5 provided compound 6 and compound HH027, respectively. Finally, removal of the Boc-protecting group of 6 proceeded smoothly, giving high yield of compound HH025.

Alternatively, palladium-catalyzed Heck coupling reactions of tert-butyl allylcarbamate with 3a or 3b gave corresponding alkenes 7a and 7b. The 2,5-dimethylpyrrole protecting groups of 7a and 7b were removed with $NH_2OH \cdot HCl$ at 100° C. to generate amines 8a and 8b in moderate yields. Finally, catalytic hydrogenation and removal of the Boc-protecting group proceeded smoothly, giving high yields of compounds HH026 and HH032.

With reference to Scheme 9, a synthetic route for compounds such as HH030 and HH006 (FIG. 5) is described below.

Scheme 9.

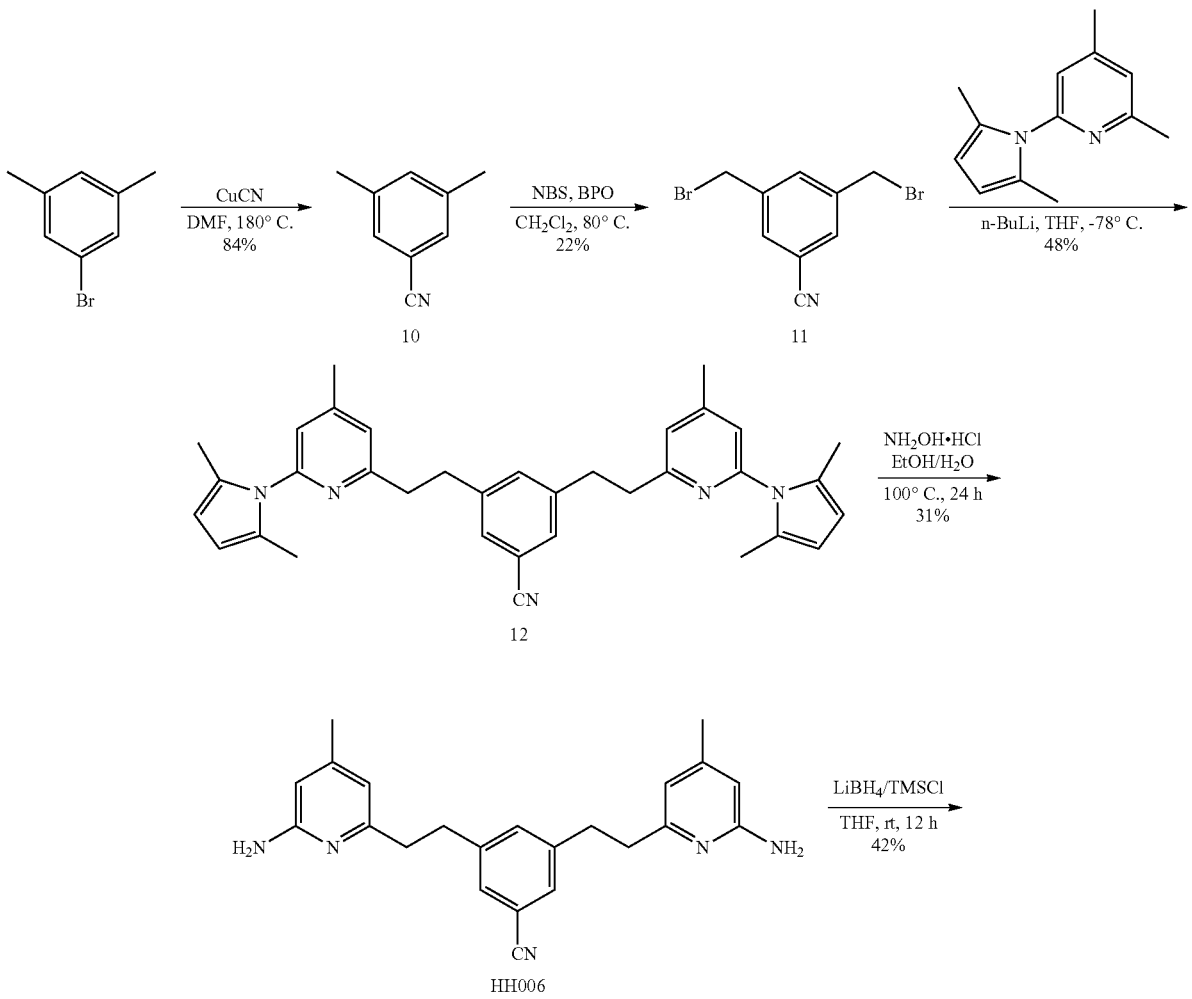

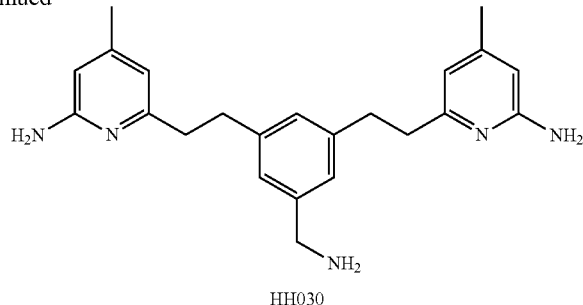

HH030

1-Bromo-3,5-dimethylbenzene was subjected to cyanation with CuCN, and subsequent bromination with NBS to afford 3,5-bis(bromomethyl)benzonitrile 11 in a 22% yield. 2-2,5-Dimethyl-1H-pyrrol-1-yl)-4,6-dimethylpyridine was treated with n-butyllithium then reacted with 11 to provide 12 in a 48% yield. The 2,5-dimethylpyrrole protecting groups of 12 were removed with $NH_2OH \cdot HCl$ at 100° C. to generate compound HH006 in a moderate yield. Alternatively, reduction of the cyano group of HH006 gave compound HH030.

Each free base inhibitor compound can be converted to the corresponding hydrochloride salt by the following general procedure: a solution of the free base methanol is treated with 4M HCl solution in methanol (10 equiv) dropwise at room temperature. The resulting mixture is stirred for 30 min. and concentrated to dryness.

As above, the activities of the target compounds of Schemes 8-9 were determined against three NOS isozymes: rat nNOS, bovine eNOS and marine iNOS using known literature methods. (Hevel, J. M.; Marletta, M. A. Nitric-oxide synthase assays. *Method Enzymol.* 1994, 233, 250-258.) The results are provided in Table 4.

TABLE 4

Inhibition of NOS isozymes.

| No. | Ki (µM) | | | Selectivity | |
| --- | --- | --- | --- | --- | --- |
| | nNOS | eNOS | iNOS | n/e | n/i |
| HH025 | 2.10 | 63.2 | 36.7 | 30 | 17 |
| HH027 | 5.75 | 97.4 | 138.0 | 17 | 24 |
| HH026 | 0.54 | 12.1 | 32.5 | 22 | 60 |
| HH032 | 0.110 | 33.4 | 21.9 | 303 | 199 |
| HH030 | 0.053 | 11.7 | 6.31 | 221 | 119 |
| HH006 | 0.056 | 26.4 | 13.4 | 472 | 239 |

As illustrated above and described in more detail, below, aminopyridine dimer compounds (e.g., cpds. 3a-n, Schemes 1-7) are provided as a novel class of inhibitors for nNOS. Without limitation, inhibitors 3g, 3h, 3j, and 3k are highly potent in a purified enzyme assay. Inhibitor 3j has shown improved bioavailability based on a cell-based assay. Moreover, substituted compound HH006 (Scheme 9) demonstrates good potency and selectivity. The structural simplicity of such components promotes a more efficient synthesis, as compared to the prior art.

EXAMPLES OF THE INVENTION

The following non-limiting examples and data illustrate various aspects and features relating to the compounds, compositions and/or methods of the present invention, including various aminopyridine dimer compounds, as are available through the synthetic methodologies described herein. In comparison with the prior art, the present compounds, compositions and/or methods provide results and data which are surprising, unexpected and contrary thereto. While the utility of this invention is illustrated through the use of several compounds and linker moieties thereof, it will be understood by those skilled in the art that comparable results are obtainable with various other compounds and/or linker moieties, as are commensurate with the scope of this invention. Likewise, while various compounds are described as isolated as an amino-protected compound and/or a mono-salt thereof, it will be understood in the art that compounds of this invention can comprise a corresponding free amine and/or a multi-salt compound, with corresponding variation in formula, structure and mass. Further, as demonstrated by the preceding synthetic schemes, the modular design of such compounds allows structural variation by choice of terminal ring and/or linker moieties. For instance, substituted (e.g., amino, halogen, $C_1$-about $C_6$ alkyl, aminoalkyl and haloalkyl, nitrile, etc.) naphthyl, phenyl and pyridinyl moieties can be incorporated into such compounds through the corresponding bis (bromomethyl) linker precursor, using synthetic techniques of the sort known in the literature or described herein or straight-forward modifications thereof as would be understood in the art, such precursors limited only by available starting materials.

General Methods. All experiments were conducted under anhydrous conditions in an atmosphere of argon, using flame-dried apparatus and employing standard techniques in handling air-sensitive materials. All solvents were distilled and stored under an argon or nitrogen atmosphere before using. All reagents were used as received. Aqueous solutions of sodium bicarbonate, sodium chloride (brine), and ammonium chloride were saturated. Analytical thin layer chromatography was visualized by ultraviolet light, ninhydrin, or phosphomolybdic acid (PMA). Flash column chromatography was carried out under a positive pressure of nitrogen. $^1$H NMR spectra were recorded on 500 MHz spectrometers. Data are presented as follows: chemical shift (in ppm on the δ scale relative to δ=0.00 ppm for the protons in TMS), integration, multiplicity (s=singlet, d=doublet, t=triplet, q=quartet, m=multiplet, br=broad), coupling constant (J/Hz). Coupling constants were taken directly from the spectra and are uncorrected. $^{13}$C NMR spectra were recorded at 125 MHz, and all chemical shift values are reported in ppm on the δ scale with an internal reference of δ 77.0 or 49.0 for $CDCl_3$ or MeOD, respectively. High-resolution mass spectra were measured by liquid chromatography/time-of-flight mass spectrometry (LC-TOF).

Example 1

General Method A: Synthesis of 2,5-dimethylpyrrole-protected inhibitors 6b-6m. To a solution of 7 (500 mg, 2.5 mmol) in THF (10 mL) at −78° C. was added n-BuLi (1.6 M solution in hexanes, 1.64 mL, 2.63 mmol) dropwise. The resulting dark red solution after the addition was transferred to an ice-bath. After 30 min, a solution of bis-bromide 5a, 5b, 5c, or 5d (1 M in THF) was added dropwise until the dark red color disappeared. (See, Momenteau, M.; Mispelter, J.; Loock, B.; Lhoste, J. M. *J. Chem. Soc. Perkin Trans.* 1 1985, 1, 61-70, incorporated herein by reference, for a general synthetic technique for bis-bromide preparation.) The reaction mixture was allowed to stir at 0° C. for an additional 10 min then quenched with $H_2O$ (20 μL). The solvent was removed by rotary evaporation, and the resulting yellow oil was purified by flash chromatography (EtOAc/hexanes) to yield 2,5-dimethylpyrrole-protected inhibitors 6b-6m.

Example 2

General Method B: Synthesis of inhibitors 3a-3m. To a solution of 6a-6m (0.5 mmol) in EtOH (10 mL) was added hydroxylamine hydrochloride ($NH_2OH \cdot HCl$, 340 mg, 5 mmol) followed by $H_2O$ (5 mL). The reaction mixture was heated at 100° C. for 20 h. After cooling to room temperature, the reaction mixture was partitioned between $Et_2O$ (50 mL) and 2 N NaOH (25 mL). The aqueous layer was extracted with $Et_2O$ (2×25 mL), and the combined organic layers were dried over $Na_2SO_4$. The solvent was removed by rotary evaporation, and the resulting yellow oil was purified by flash chromatography (5-10% MeOH in $CH_2Cl_2$) to yield inhibitors 3a-3m.

Example 3

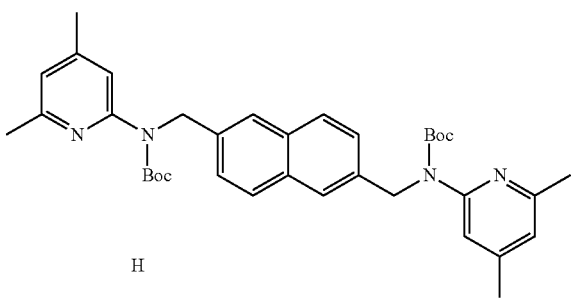

Chemical Formula: $C_{36}H_{45}N_4O_4$
Exact Mass: 597.34408

Di-tert-butyl naphthalene-2,6-diylbis(methylene)bis(4,6-dimethylpyridin-2-ylcarbamate) (6a). To a solution of 4 (444 mg, 2 mmol) in DMF (10 mL) at 0° C. was added NaH (60% in mineral oil, 88 mg, 2.2 mmol). After 15 min, bis-bromide 5a (314 mg, 1 mmol) was added slowly. The reaction mixture was allowed to stir at room temperature for 6 h then concentrated. The crude product was purified by flash column chromatography (EtOAc/hexanes, 1:9-1:4) to yield 6a (960 mg, 81%) as a white solid: $^1$H NMR (500 MHz, $CDCl_3$) δ 1.41 (s, 18H), 2.29 (s, 6H), 2.45 (s, 6H), 5.33 (s, 4H), 6.72 (s, 2H), 7.28 (s, 2H), 7.42-7.44 (d, J=8.5 Hz, 2H), 7.68-7.70 (m, 4H); $^{13}$C NMR (125 MHz, $CDCl_3$) δ14.4, 21.3, 24.4, 28.5, 31.9, 50.5, 81.2, 117.7, 120.6, 126.1, 126.3, 127.8, 132.6, 137.1, 148.7, 154.0, 154.7, 156.5; ESI (M+H$^+$) calcd for $C_{36}H_{45}N_4O_4$ 597.34408, found 597.34492.

Example 4

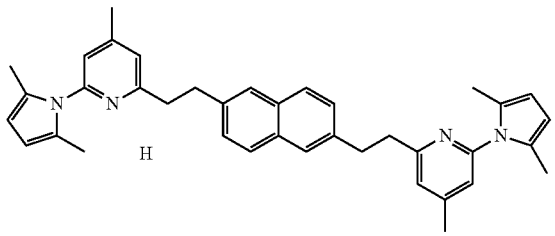

Chemical Formula: $C_{38}H_{41}N_4$
Exact Mass: 553.33312

2,6-Bis(2-(6-(2,5-dimethyl-1H-pyrrol-1-yl)-4-methylpyridin-2-yl)ethyl)naphthalene (6b). Compound 6b was synthesized starting with 7 and 5a using general method A (90%): $^1$H NMR (500 MHz, $CDCl_3$) δ 2.18 (s, 12H), 2.39 (s, 6H), 3.20-3.40 (m, 8H), 5.94 (s, 4H), 6.90 (s, 2H), 6.97 (s, 2H), 7.34-7.36 (d, J=8.5 Hz, 2H), 7.61 (s, 2H), 7.69-7.71 (d, J=8.5 Hz, 2H); $^{13}$C NMR (125 MHz, $CDCl_3$) δ 13.5, 21.3, 36.2, 39.9, 107.0, 120.4, 122.9, 126.6, 127.6, 127.7, 128.8, 132.5, 138.6, 149.7, 151.9, 161.2; ESI (M+H$^+$) calcd for $C_{38}H_{41}N_4$ 553.33312, found 553.33382.

Example 5

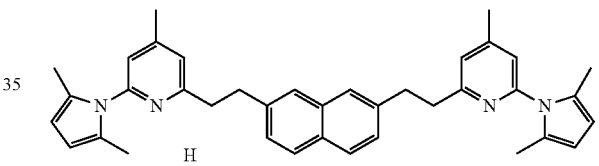

Chemical Formula: $C_{38}H_{41}N_4$
Exact Mass: 553.33312

2,7-Bis(2-(6-(2,5-dimethyl-1H-pyrrol-1-yl)-4-methylpyridin-2-yl)ethyl)naphthalene (6c). Compound 6c was synthesized starting with 7 and 5b using general method A (55%): $^1$H NMR (500 MHz, $CDCl_3$) δ 2.18 (s, 12H), 2.39 (s, 6H), 3.15-3.25 (m, 8H), 5.94 (s, 4H), 6.90 (s, 2H), 6.98 (s, 2H), 7.32-7.34 (d, J=8.5 Hz, 2H), 7.57 (s, 2H), 7.75-7.76 (d, J=8.5 Hz, 2H); $^{13}$C NMR (125 MHz, $CDCl_3$) δ 13.5, 21.3, 36.3, 39.9, 107.0, 120.4, 122.9, 126.4, 126.9, 127.9, 128.8, 130.9, 134.1, 139.4, 149.7, 151.9, 161.2; ESI (M+H$^+$) calcd for $C_{38}H_{41}N_4$ 553.33312, found 553.33379.

Example 6

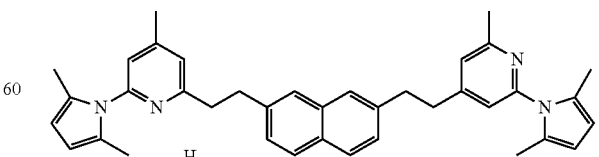

Chemical Formula: $C_{38}H_{41}N_4$
Exact Mass: 553.33312

2-(2,5-Dimethyl-1H-pyrrol-1-yl)-4-(2-(7-(2-(6-(2,5-dimethyl-1H-pyrrol-1-yl)-4-methylpyridin-2-yl)ethyl)naphthalen-2-yl)ethyl)-6-methylpyridine (6d). Inhibitor 6d was synthesized starting with 7 and 5b using general method A (55%): $^1$H NMR (500 MHz, CDCl$_3$) δ 2.02 (s, 6H), 2.16 (s, 6H), 2.36 (s, 3H), 2.57 (s, 3H), 3.00-3.15 (m, 4H), 3.15-3.30 (m, 4H), 5.86 (s, 2H), 5.93 (s, 2H), 6.79 (s, 1H), 6.88 (s, 1H), 6.96 (s, 1H), 7.03 (s, 1H), 7.25-7.27 (d, J=10 Hz, 1H), 7.31-7.33 (d, J=10 Hz, 1H), 7.47 (s, 1H), 7.54 (s, 1H), 7.73-7.74 (d, J=9.0 Hz, 2H); $^{13}$C NMR (125 MHz, CDCl$_3$) δ 13.2, 13.5, 21.2, 24.5, 36.2, 36.98, 37.02, 39.9, 106.8, 107.0, 119.5, 120.4, 122.5, 122.9, 126.4, 126.5, 126.6, 127.2, 127.9, 128.1, 128.6, 128.7, 131.0, 134.0, 138.2, 139.6, 149.8, 151.7, 151.9, 153.1, 158.5, 161.1; ESI (M+H$^+$) calcd for C$_{38}$H$_{41}$N$_4$ 553.33312, found 553.33296.

Example 7

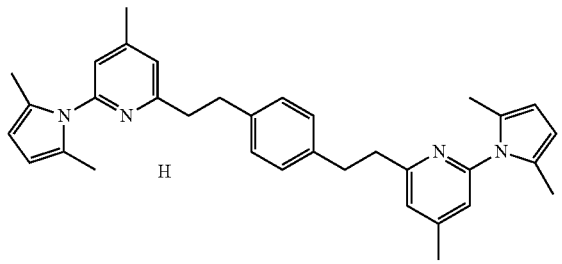

Chemical Formula: C$_{34}$H$_{39}$N$_4$
Exact Mass: 503.31747

1,4-Bis(2-(6-(2,5-dimethyl-1H-pyrrol-1-yl)-4-methylpyridin-2-yl)ethyl)benzene (6e). Compound 6e was synthesized starting with 7 and 5c using general method A (65%): $^1$H NMR (500 MHz, CDCl$_3$) δ 2.21 (s, 12H), 2.44 (s, 6H), 3.12-3.15 (m, 8H), 5.97 (s, 4H), 6.94 (s, 2H), 7.01 (s, 2H), 7.18 (s, 4H); $^{13}$C NMR (125 MHz, CDCl$_3$) δ 13.6, 21.3, 35.8, 40.1, 107.0, 120.3, 122.9, 128.8, 139.4, 149.7, 151.9, 161.4; ESI (M+H$^+$) calcd for C$_{34}$H$_{39}$N$_4$ 503.31747, found 503.31828.

Example 8

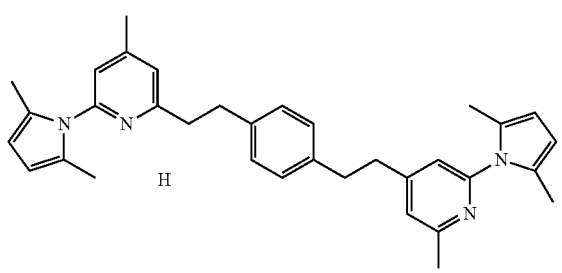

Chemical Formula: C$_{34}$H$_{39}$N$_4$
Exact Mass: 503.31747

2-(2,5-Dimethyl-1H-pyrrol-1-yl)-4-(4-(2-(6-(2,5-dimethyl-1H-pyrrol-1-yl)-4-methylpyridin-2-yl)ethyl)phenethyl)-6-methylpyridine (6F). Inhibitor 6f was synthesized starting with 7 and 5c using general method A (35%): $^1$H NMR (500 MHz, CDCl$_3$) δ 2.12 (s, 6H), 2.19 (s, 6H), 2.43 (s, 3H), 2.61 (s, 3H), 2.99 (s, 4H), 3.05-3.20 (s, 4H), 5.91 (s, 2H), 5.95 (s, 2H), 6.83 (s, 1H), 6.92 (s, 1H), 6.99 (s, 1H), 7.04 (s, 1H), 7.10-7.12 (d, J=8.0 Hz, 2H), 7.16-7.18 (d, J=7.5, 2H); $^{13}$C NMR (125 MHz, CDCl$_3$) δ 13.4, 13.5, 21.3, 24.5, 35.7, 36.4, 37.2, 40.1, 106.9, 107.0, 119.5, 120.3, 122.5, 122.8, 128.67, 128.70, 128.73, 128.9, 138.3, 139.8, 149.7, 151.7, 151.9, 153.3, 158.5, 161.3; ESI (M+H$^+$) calcd for C$_{34}$H$_{39}$N$_4$ 503.31747, found 503.31845.

Example 9

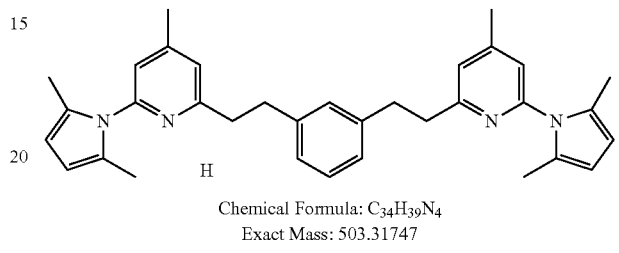

Chemical Formula: C$_{34}$H$_{39}$N$_4$
Exact Mass: 503.31747

1,3-Bis(2-(6-(2,5-dimethyl-1H-pyrrol-1-yl)-4-methylpyridin-2-yl)ethyl)benzene (6g). Inhibitor 6g was synthesized starting with 7 and 5d using general method A (60%): $^1$H NMR (500 MHz, CDCl$_3$) δ 2.19 (s, 12H), 2.42 (s, 6H), 3.00-3.20 (m, 8H), 5.94 (s, 4H), 6.91 (s, 2H), 6.97 (s, 2H), 7.06-7.08 (m, 3H), 7.21-7.23 (m, 1H); $^{13}$C NMR (125 MHz, CDCl$_3$) δ 13.5, 21.7, 36.2, 40.1, 107.0, 120.3, 122.9, 126.4, 128.68, 128.74, 129.0, 141.9, 149.7, 151.9, 161.3; ESI (M+H$^+$) calcd for C$_{34}$H$_{39}$N$_4$ 503.31747. found 503.31814.

Example 10

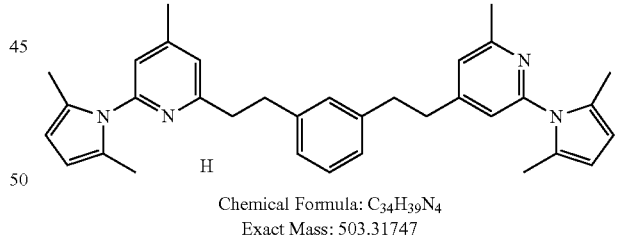

Chemical Formula: C$_{34}$H$_{39}$N$_4$
Exact Mass: 503.31747

2-(2,5-Dimethyl-1H-pyrrol-1-yl)-4-(3-(2-(6-(2,5-dimethyl-1H-pyrrol-1-yl)-4-methylpyridin-2-yl)ethyl)phenethyl)-6-methylpyridine (6h). Inhibitor 6h was synthesized starting with 7 and 5d using general method A (35%): $^1$H NMR (500 MHz, CDCl$_3$) δ 2.12 (s, 6H), 2.19 (s, 6H), 2.41 (s, 3H), 2.60 (s, 3H), 2.97 (s, 4H), 3.05-3.20 (m, 4H), 5.91 (s, 2H), 5.94 (s, 2H), 6.83 (s, 1H), 6.91 (s, 1H), 6.97 (s, 1H), 7.02 (s, 1H), 7.05-7.15 (m, 3H), 7.21-7.25 (m, 1H); $^{13}$C NMR (125 MHz, CDCl$_3$) δ 13.4, 13.5, 21.2, 24.5, 36.1, 36.8, 37.2, 40.1, 106.9, 107.0, 119.4, 120.3, 122.5, 122.8, 126.3, 126.7, 128.65, 128.71, 128.8, 128.9, 140.8, 142.1, 149.8, 151.7, 151.9, 153.2, 158.5, 161.2; ESI (M+H⁺) calcd for $C_{34}H_{39}N_4$ 503.31747, found 503.31840.

Example 11

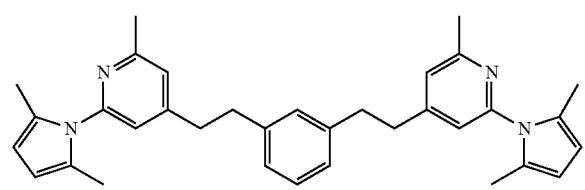

Chemical Formula: $C_{34}H_{39}N_4$
Exact Mass: 503.31747

1,3-Bis(2-(2-(2,5-dimethyl-1H-pyrrol-1-yl)-6-methylpyridin-4-yl)ethyl)benzene (6i). To a solution of 7 (500 mg, 2.5 mmol) in THF (10 mL) at 0° C. was added lithium diisopropylamide (2.0 M solution in THF, 1.32 mL, 2.63 mmol) dropwise. The resulting dark red solution after the addition was allowed to warm to room temperature. After 30 min, a solution of bromide 5d (1 M in THF) was added dropwise until the dark red color disappeared. The reaction mixture was allowed to stir at 0° C. for an additional 10 min then quenched with H₂O (20 μL). The solvent was removed by rotary evaporation, and the resulting yellow oil was purified by flash chromatography (EtOAc/hexanes, 1:9) to yield 2,5-dimethylpyrrole-protected inhibitors 6i (405 mg, 65%): $^1$H NMR (500 MHz, CDCl₃) δ 2.09 (s, 12H), 2.56 (s, 6H), 2.94 (s, 6H), 5.88 (s, 3H), 6.81 (s, 1H), 6.95-7.05 (m, 4H), 7.20-7.23 (m, 1H); $^{13}$C NMR (125 MHz, CDCl₃) δ 13.4, 24.5, 36.7, 37.1, 106.9, 119.3, 122.4, 126.6, 128.6, 128.8, 141.0, 151.8, 153.1, 158.5; ESI (M+H⁺) calcd for $C_{34}H_{39}N_4$ 503.31747, found 503.31801.

Example 12

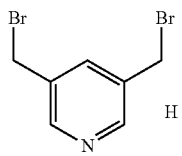

Chemical Formula: $C_7H_8Br_2N$
Exact Mass: 263.90235

3,5-Bis(bromomethyl)pyridine. To pyridine-3,5-diyldimethanol (2 g, 14 mmol) was added 60% HBr (15 mL) slowly. The reaction was heated at 125° C. for 6 h then cooled to room temperature. The resulting residue was dissolved in H₂O (50 mL) to give a yellow solution. To this solution was added saturated NaHCO₃ to pH 8. The resulting aqueous solution was extracted with CH₂Cl₂ (4×50 mL), and the combined organic layers were dried over Na₂SO₄. The solvent was removed by rotary evaporation, and the resulting material was purified by flash column chromatography (EtOAc/hexanes, 1:4) to yield 3,5-bis(bromomethyl)pyridine (3.5 g, 95%) as a white solid: $^1$H NMR (500 MHz, CDCl₃) δ 4.45 (s, 4H), 7.74-7.75 (t, J=2.0 Hz, 1H), 8.53-8.54 (d, J=2.0 Hz, 2H); $^{13}$C NMR (125 MHz, CDCl₃) δ 29.3, 134.0, 137.3, 149.8; LC-TOF (M+H⁺) calcd for $C_7H_8Br_2N$ 263.90235. found 263.90182.

Example 13

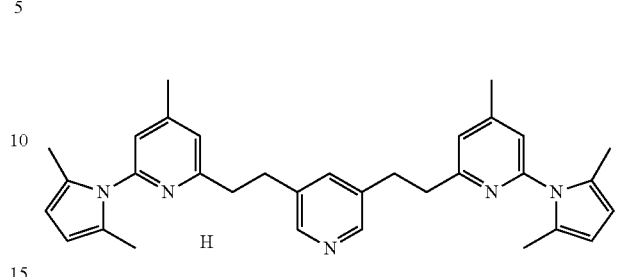

Chemical Formula: $C_{33}H_{38}N_5$
Exact Mass: 504.31272

3,5-Bis(2-(6-(2,5-dimethyl-1H-pyrrol-1-yl)-4-methylpyridin-2-yl)ethyl)pyridine (6j). Compound 6j was synthesized starting with 7 and 5e using general method A (55%): $^1$H NMR (500 MHz, CDCl₃) δ 2.13 (s, 12H), 2.38 (s, 6H), 3.05 (s, 8H), 5.90 (s, 4H), 6.88 (s, 2H), 6.91 (s, 2H), 7.34 (s, 1H), 8.21-8.22 (d, J=2.5 Hz, 2H); $^{13}$C NMR (125 MHz, CDCl₃) δ 13.5, 21.2, 32.8, 39.4, 107.0, 120.5, 122.9, 128.6, 136.2, 136.5, 147.9, 149.8, 152.0, 160.3; LC-TOF (M+H⁺) calcd for $C_{33}H_{38}N_5$ 504.31272, found 504.31265.

Example 14

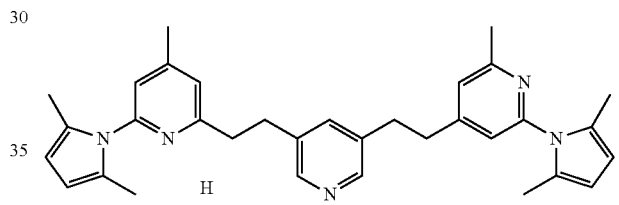

Chemical Formula: $C_{33}H_{38}N_5$
Exact Mass: 504.31272

2-(2,5-Dimethyl-1H-pyrrol-1-yl)-4-(2-(5-(2-(6-(2,5-dimethyl-1H-pyrrol-1-yl)-4-methylpyridin-2-yl)ethyl)pyridin-3-yl)ethyl)-6-methylpyridine (6k). Compound 6k was synthesized starting with 7 and 5e using general method A (30%): $^1$H NMR (500 MHz, CDCl₃) δ 2.08 (s, 6H), 2.13 (s, 6H), 2.38 (s, 3H), 2.56 (s, 3H), 2.94 (s, 4H), 3.06 (s, 4H), 5.88 (s, 2H), 5.91 (s, 2H), 6.80 (s, 1H), 6.89 (s, 1H), 6.92 (s, 1H), 6.97 (s, 1H), 7.31 (s, 1H), 8.25 (s, 1H), 8.29 (s, 1H); $^{13}$C NMR (125 MHz, CDCl₃) δ 13.4, 13.5, 21.2, 24.5, 32.8, 33.8, 36.7, 39.4, 107.0, 119.2, 120.6, 122.3, 122.9, 128.60, 128.66, 128.69, 135.6, 136.2, 136.8, 149.88, 149.93, 151.9, 152.0, 152.3, 158.8, 160.3; LC-TOF (M+H⁺) calcd for $C_{33}H_{38}N_5$ 504.31272, found 504.31236.

Example 15

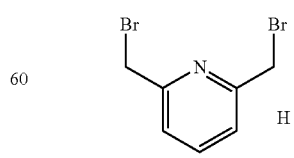

Chemical Formula: $C_7H_8Br_2N$
Exact Mass: 263.90235

2,6-Bis(bromomethyl)pyridine. To pyridine-2,6-diyldimethanol (2 g, 14 mmol) was added 60% HBr (15 mL) slowly. The reaction was heated at 125° C. for 6 h then cooled to room temperature. The resulting residue was dissolved in H$_2$O (50 mL) to give a yellow solution. To this solution was added saturated NaHCO$_3$ to pH 8. The resulting aqueous solution was extracted with CH$_2$Cl$_2$ (4×50 mL), and the combined organic layers were dried over Na$_2$SO$_4$. The solvent was removed by rotary evaporation, and the resulting material was purified by flash column chromatography (EtOAc/hexanes, 1:9-1:4) to yield 2,6-bis(bromomethyl)pyridine (3.5 g, 96%) as a white solid: $^1$H NMR (500 MHz, CDCl$_3$) δ 4.53 (s, 4H), 7.36-7.38 (d, J=8.0 Hz, 2H), 7.68-7.71 (dd, J=7.5, 8.0 Hz, 1H); $^{13}$C NMR (125 MHz, CDCl$_3$) δ 33.8, 123.1, 138.4, 157.0; LC-TOF (M+H$^+$) calcd for C$_7$H$_8$Br$_2$N 263.90235. found 263.90193.

Example 16

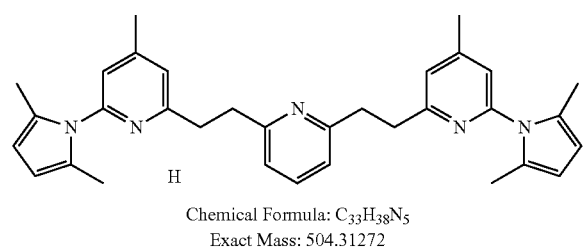

Chemical Formula: C$_{33}$H$_{38}$N$_5$
Exact Mass: 504.31272

2,6-Bis(2-(6-(2,5-dimethyl-1H-pyrrol-1-yl)-4-methylpyridin-2-yl)ethyl)pyridine (6l). Compound 6l was synthesized starting with 7 and 5f using general method A (58%): $^1$H NMR (500 MHz, CDCl$_3$) δ 2.08 (s, 12H), 2.37 (s, 6H), 3.25 (s, 8H), 5.91 (s, 4H), 6.85-6.87 (d, J=9.5 Hz, 2H), 6.93-6.95 (d, J=7.5 Hz, 2H), 7.00 (s, 2H), 7.42-7.46 (dd, J=7.5, 8.0 Hz, 1H); $^{13}$C NMR (125 MHz, CDCl$_3$) δ 13.5, 21.2, 37.9, 38.1, 106.9, 120.2, 120.5, 122.9, 128.7, 136.7, 149.6, 151.8, 160.8, 161.3; LC-TOF (M+H$^+$) calcd for C$_{33}$H$_{38}$N$_5$ 504.31272, found 504.31262.

Example 17

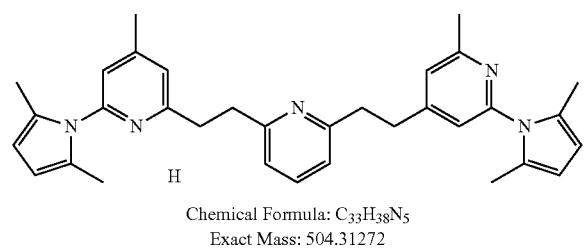

Chemical Formula: C$_{33}$H$_{38}$N$_5$
Exact Mass: 504.31272

2-(2,5-Dimethyl-1H-pyrrol-1-yl)-4-(2-(6-(2-(6-(2,5-dimethyl-1H-pyrrol-1-yl)-4-methylpyridin-2-yl)ethyl)pyridin-2-yl)ethyl)-6-methylpyridine (6m). Compound 6m was synthesized starting with 7 and 6f using general method A (37%): $^1$H NMR (500 MHz, CDCl$_3$) δ 2.07 (s, 6H), 2.11 (s, 6H), 2.37 (s, 3H), 2.55 (s, 3H), 3.10-3.12 (t, J=3.0 Hz, 4H), 3.21-3.23 (t, J=3.0 Hz, 4H), 5.87 (s, 2H), 5.90 (s, 2H), 6.80-7.10 (m, 6H), 7.40-7.50 (m, 1H); $^{13}$C NMR (125 MHz, CDCl$_3$) δ 13.3, 13.5, 21.2, 24.4, 34.98, 35.041, 37.9, 38.08, 38.15, 38.8, 106.9, 119.3, 120.3, 120.5, 120.8, 122.4, 122.8, 122.9, 128.6, 128.7, 136.9, 149.6, 151.8, 153.2, 153.3, 158.4, 159.7, 160.8, 161.1, 161.3; LC-TOF (M+H$^+$) calcd for C$_{33}$H$_{38}$N$_5$ 504.31272, found 504.31226.

Example 18

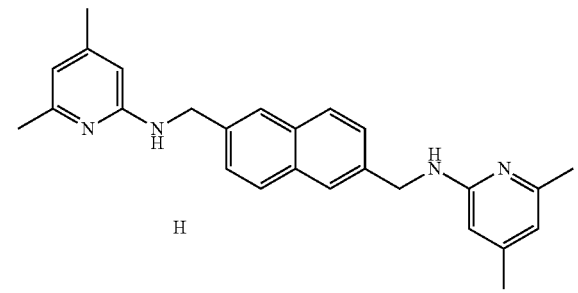

Chemical Formula: C$_{26}$H$_{29}$N$_4$
Exact Mass: 397.23922

N,N'-(Naphthalene-2,6-diylbis(methylene))bis(4,6-dimethylpyridin-2-amine) (3a). To a solution of 6a (590 mg, 1.0 mmol) in CH$_2$Cl$_2$ (8 mL) was added trifluoroacetic acid (TFA, 8 mL). The reaction mixture was allowed to stir at room temperature for 8 h then was concentrated. The crude product was purified by flash column chromatography (2-5% MeOH in CH$_2$Cl$_2$) to yield 3a (355 mg, 90%) as a white solid: $^1$H NMR (500 MHz, CD$_3$OD/CDCl$_3$) δ 2.28 (s, 6H), 2.48 (s, 6H), 4.60 (s, 4H), 6.46 (s, 4H), 7.45-7.47 (d, J=8.5, 2H), 7.78 (s, 2H), 7.84-7.86 (d, J=8.5, 2H); $^{13}$C NMR (125 MHz, CD$_3$OD/CDCl$_3$) δ 18.6, 22.0, 45.9, 106.8, 114.5, 125.6, 129.0, 133.1, 134.3, 147.6, 153.8, 158.0; ESI (M+H$^+$) calcd for C$_{26}$H$_{29}$N$_4$ 397.23922, found 397.23999.

Example 19

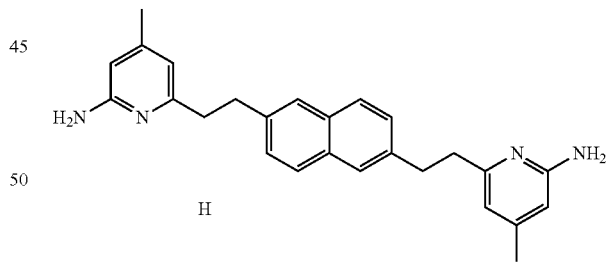

Chemical Formula: C$_{26}$H$_{29}$N$_4$
Exact Mass: 397.23922

6,6'-(2,2'-(Naphthalene-2,6-diyl)bis(ethane-2,1-diyl))bis(4-methylpyridin-2-amine) (3b). Inhibitor 3b was synthesized using general method B (90%): $^1$H NMR (500 MHz, CDCl$_3$) δ 2.19 (s, 6H), 2.94-2.98 (dd, J=7.5, 10.5 Hz, 4H), 3.12-3.16 (dd, J=6.0, 9.0 Hz, 4H), 4.52 (br s, 4H), 6.20 (s, 2H), 6.37 (s, 2H), 7.35-7.36 (d, J=8.5 Hz, 2H), 7.64 (s, 2H), 7.70-7.72 (d, J=8.5 Hz, 2H); $^{13}$C NMR (125 MHz, CDCl$_3$) δ 21.2, 36.4, 40.0, 106.9, 115.7, 126.4, 127.6, 132.4, 139.0, 149.6, 158.5, 159.6; ESI (M+H$^+$) calcd for C$_{26}$H$_{29}$N$_4$ 397.23922, found 397.23954.

Example 20

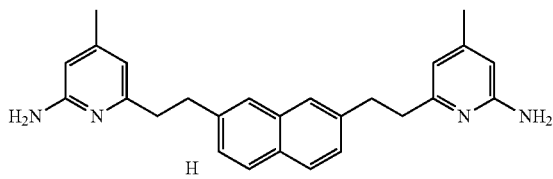

Chemical Formula: $C_{26}H_{29}N_4$
Exact Mass: 397.23922

6,6'-(2,2'-(Naphthalene-2,7-diyl)bis(ethane-2,1-diyl))bis(4-methylpyridin-2-amine) (3c). Inhibitor 3c was synthesized using general method B (90%): $^1$H NMR (500 MHz, CDCl$_3$) δ 2.18 (s, 6H), 2.95-2.99 (m, 4H), 2.13-2.17 (m, 4H), 4.55 (br s, 4H), 6.18 (s, 2H), 6.38 (s, 2H), 7.32-7.33 (d, J=8.5 Hz, 2H), 7.60 (s, 2H), 7.72-7.74 (d, J=8.0 Hz, 2H); $^{13}$C NMR (125 MHz, CDCl$_3$) δ 21.2, 36.5, 40.0, 106.8, 114.6, 126.3, 126.9, 127.8, 130.8, 134.1, 139.8, 149.5, 158.6, 159.7; ESI (M+H$^+$) calcd for $C_{26}H_{29}N_4$ 397.23922, found 397.23946.

Example 21

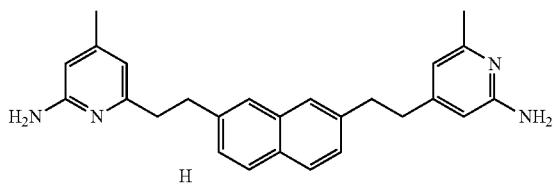

Chemical Formula: $C_{26}H_{29}N_4$
Exact Mass: 397.23922

4-(2-(7-(2-(6-Amino-4-methylpyridin-2-yl)ethyl)naphthalen-2-yl)ethyl)-6-methylpyridin-2-amine (3d). Inhibitor 3d was synthesized using general method B (90%): 1H NMR (500 MHz, CDCl$_3$) δ 2.19 (s, 3H), 2.37 (s, 3H), 2.82-2.84 (m, 2H), 2.85-2.99 (m, 2H), 3.00-3.03 (m, 2H), 3.14-3.17 (m, 2H), 4.48 (br s, 4H), 6.16 (s, 1H), 6.19 (s, 1H), 6.38 (s, 1H), 6.43 (s, 1H), 7.25-7.27 (d, J=8.5 Hz, 1H), 7.33-7.35 (d, J=8.5 Hz, 1H), 7.55 (s, 1H), 7.61 (s, 1H), 7.73-7.75 (d, J=8.0 Hz, 2H); $^{13}$C NMR (125 MHz, CDCl$_3$) δ 21.2, 24.3, 36.4, 36.9, 37.3, 40.0, 105.6, 106.8, 114.2, 114.6, 126.29, 126.32, 126.7, 127.1, 127.8, 127.9, 130.9, 134.0, 139.0, 140.0, 149.4, 153.1, 156.8, 158.4, 158.6, 159.7; ESI (M+H$^+$) calcd for $C_{26}H_{29}N_4$ 397.23922, found 397.23970.

Example 22

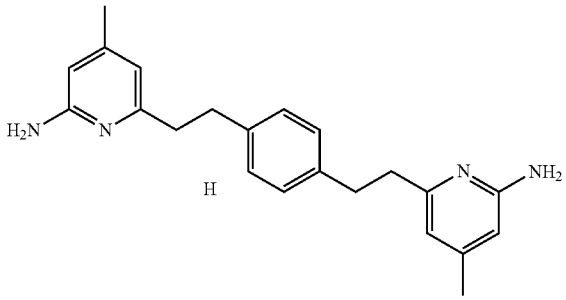

Chemical Formula: $C_{22}H_{27}N_4$
Exact Mass: 347.22357

6,6'-(2,2'-(1,4-Phenylene)bis(ethane-2,1-diyl)bis(4-methylpyridin-2-amine) (3e). Inhibitor 3e was synthesized using general method B (85%): $^1$H NMR (500 MHz, CDCl$_3$) δ 2.20 (s, 6H), 2.85-2.88 (m, 4H), 2.94-2.98 (m, 4H), 4.39 (s, 4H), 6.19 (s, 2H), 6.36 (s, 2H), 7.16 (s, 4H); $^{13}$C NMR (125 MHz, CDCl$_3$) δ 21.2, 35.9, 40.2, 106.7, 114.7, 128.6, 139.7, 149.4, 158.4, 160.0; ESI (M+H$^+$) calcd for $C_{22}H_{27}N_4$ 347.22357, found 347.22399.

Example 23

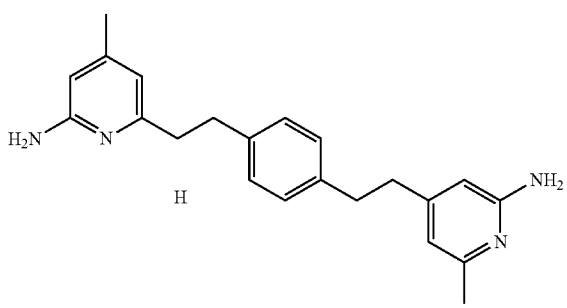

Chemical Formula: $C_{22}H_{27}N_4$
Exact Mass: 347.22357

4-(4-(2-(6-Amino-4-methylpyridin-2-yl)ethyl)phenethyl)-6-methylpyridin-2-amine (3f). Inhibitor 3f was synthesized using general method B (85%): $^1$H NMR (500 MHz, CDCl$_3$) δ 2.20 (s, 3H), 2.37 (s, 3H), 2.73-2.76 (m, 2H), 2.83-2.88 (m, 4H), 2.95-2.98 (m, 2H), 4.42 (s, 2H), 4.45 (s, 2H), 6.13 (s, 1H), 6.19 (s, 1H), 6.37 (s, 1H), 6.40 (s, 1H), 7.09-7.19 (d, J=8.0 Hz, 2H), 7.15-7.17 (d, J=8.0 Hz, 2H); $^{13}$C NMR (125 MHz, CDCl$_3$) δ 21.2, 24.2, 35.9, 36.4, 37.5, 40.2, 105.6, 106.7, 114.3, 114.6, 128.6, 128.7, 138.9, 140.0, 149.5, 153.2, 156.7, 158.3, 158.4, 159.8; ESI (M+H$^+$) calcd for $C_{22}H_{27}N_4$ 347.22357, found 347.22410.

Example 24

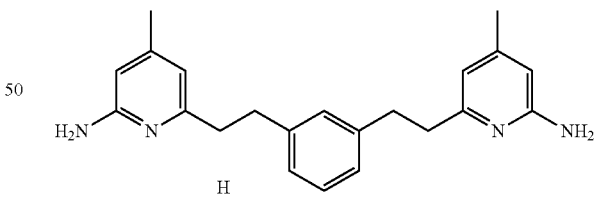

Chemical Formula: $C_{22}H_{27}N_4$
Exact Mass: 347.22357

6,6'-(2,2'-(1,3-Phenylene)bis(ethane-2,1-diyl))bis(4-methylpyridin-2-amine) (3g). Inhibitor 3g was synthesized using general method B (87%): $^1$H NMR (500 MHz, CDCl$_3$) δ 2.20 (s, 6H), 2.84-2.87 (m, 4H), 2.94-2.98 (m, 4H), 4.44 (br s, 4H), 6.19 (s, 2H), 6.35 (s, 2H), 7.06-7.11 (s, 3H), 7.19-7.22 (m, 1H); $^{13}$C NMR (125 MHz, CDCl$_3$) δ 21.2, 36.4, 40.2, 106.7, 114.6, 126.2, 128.5, 129.0, 142.2, 149.4, 158.5, 159.9; ESI (M+H$^+$) calcd for $C_{22}H_{27}N_4$ 347.22357, found 347.22402.

Example 25

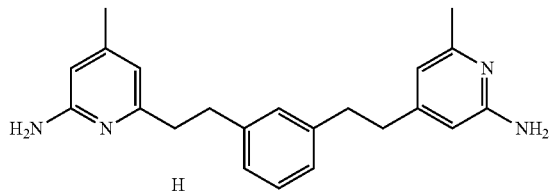

Chemical Formula: C$_{22}$H$_{27}$N$_4$
Exact Mass: 347.22357

4-(3-(2-(6-Amino-4-methylpyridin-2-yl)ethyl)phenethyl)-6-methylpyridin-2-amine (3h). Inhibitor 3h was synthesized using general method B (85%): $^1$H NMR (500 MHz, CDCl$_3$) δ 2.19 (s, 3H), 2.36 (s, 3H), 2.71-2.75 (m, 2H), 2.82-2.87 (m, 4H), 2.95-2.98 (m, 2H), 4.47 (br s, 4H), 6.13 (s, 1H), 6.19 (s, 1H), 6.35 (s, 1H), 6.38 (s, 1H), 6.99-7.01 (d, J=7.5 Hz, 1H), 7.04 (s, 1H), 7.06-7.08 (d, J=7.5 Hz, 1H), 7.19-7.22 (m, 1H); $^{13}$C NMR (125 MHz, CDCl$_3$) δ 21.2, 24.2, 36.3, 36.8, 37.4, 40.2, 105.6, 106.8, 114.2, 114.6, 126.1, 126.5, 128.6, 128.9, 141.5, 142.3, 149.5, 153.3, 156.6, 158.3, 158.5, 159.7; ESI (M+H$^+$) calcd for C$_{22}$H$_{27}$N$_4$ 347.22357, found 347.22417.

Example 26

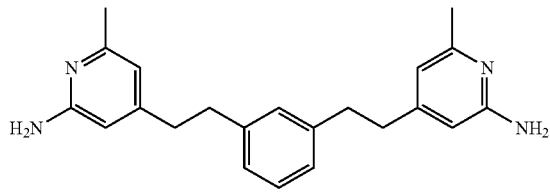

Chemical Formula: C$_{22}$H$_{27}$N$_4$
Exact Mass: 347.22357

4,4'-(2,2'-(1,3-Phenylene)bis(ethane-2,1-diyl))bis(6-methylpyridin-2-amine) (3i). Inhibitor 3i was synthesized using general method B (88%): $^1$H NMR (500 MHz, CDCl$_3$) δ 2.33 (s, 6H), 2.46 (br s, 4H), 2.69-2.72 (m, 4H), 2.81-2.84 (m, 4H), 6.10 (s, 2H), 6.35 (s, 2H), 6.91 (s, 2H), 6.99-7.00 (d, J=8.0 Hz, 2H), 7.17-7.20 (m, 1H); $^{13}$C NMR (125 MHz, CDCl$_3$) δ 23.8, 36.6, 37.4, 105.9, 114.1, 126.4, 128.7, 128.8, 141.5, 153.5, 156.1, 158.2; ESI (M+H$^+$) calcd for C$_{22}$H$_{27}$N$_4$ 347.22357, found 347.22389.

Example 27

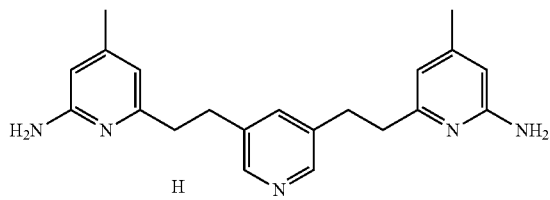

Chemical Formula: C$_{21}$H$_{26}$N$_5$
Exact Mass: 348.21882

6,6'-(2,2'-(Pyridine-3,5-diyl)bis(ethane-2,1-diyl))bis(4-methylpyridin-2-amine) (3j). Inhibitor 3j was synthesized using general method B (85%): $^1$H NMR (500 MHz, CDCl$_3$) δ 2.16 (s, 6H), 2.80-2.83 (m, 4H), 2.93-2.96 (m, 4H), 4.47 (br s, 4H), 6.17 (s, 2H), 6.27 (s, 2H), 7.31 (s, 1H), 8.26-8.27 (d, J=1.5 Hz, 2H); $^{13}$C NMR (125 MHz, CDCl$_3$) δ 21.2, 33.1, 39.6, 106.9, 114.7, 136.3, 136.8, 147.79, 147.82, 149.5, 158.6, 158.9; LC-TOF (M+H$^+$) calcd for C$_{21}$H$_{26}$N$_5$ 348.21882, found 348.21890.

Example 28

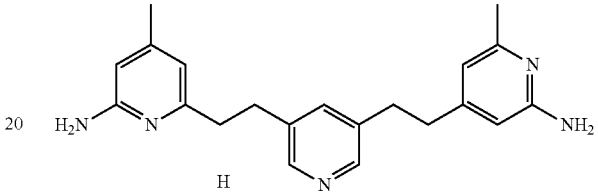

Chemical Formula: C$_{21}$H$_{26}$N$_5$
Exact Mass: 348.21882

4-(2-(5-(2-(6-Amino-4-methylpyridin-2-yl)ethyl)pyridin-3-yl)ethyl)-6-methylpyridin-2-amine (3k). Inhibitor 3k was synthesized using general method B (81%): $^1$H NMR (500 MHz, CDCl$_3$) δ 2.18 (s, 3H), 2.36 (s, 3H), 2.69-2.73 (m, 2H), 2.82-2.85 (m, 4H), 2.94-2.98 (m, 2H), 4.46 (br s, 2H), 4.53 (br s, 2H), 6.09 (s, 1H), 6.19 (s, 1H), 6.31 (s, 1H), 6.35 (s, 1H), 7.27 (s, 1H), 8.26-8.29 (m, 2H); $^{13}$C NMR (125 MHz, CDCl$_3$) δ 21.2, 24.2, 33.0, 33.1, 33.7, 37.0, 39.5, 105.6, 107.0, 114.1, 114.7, 136.1, 136.3, 136.8, 136.9, 147.7, 147.8, 148.1, 149.5, 149.6, 152.4, 156.8, 158.3, 158.5, 158.7, 158.8; LC-TOF (M+H$^+$) calcd for C$_{21}$H$_{26}$N$_5$ 348.21882, found 348.21878.

Example 29

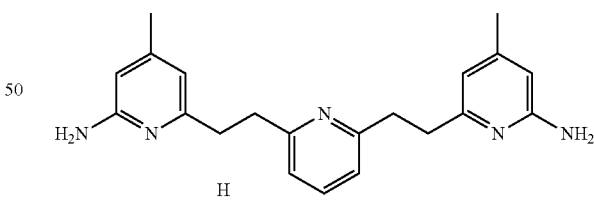

Chemical Formula: C$_{21}$H$_{26}$N$_5$
Exact Mass: 348.21882

6,6'-(2,2'-(Pyridine-2,6-diyl)bis(ethane-2,1-diyl))bis(4-methylpyridin-2-amine) (3l). Inhibitor 3l was synthesized using general method B (80%): $^1$H NMR (500 MHz, CDCl$_3$) δ 2.14 (s, 6H), 2.97-3.01 (m, 4H), 3.13-3.16 (m, 4H), 4.68 (br s, 4H), 6.15 (s, 2H), 6.34 (s, 2H), 6.93-6.95 (d, J=7.5 Hz, 2H), 7.41-7.44 (dd, J=7.5, 7.5 Hz, 1H); $^{13}$C NMR (125 MHz, CDCl$_3$) δ 21.2, 38.2, 38.5, 106.7, 114.5, 120.3, 136.6, 149.3, 158.6, 159.7, 161.1; LC-TOF (M+H$^+$) calcd for C$_{21}$H$_{26}$N$_5$ 348.21882, found 348.21871.

Example 30

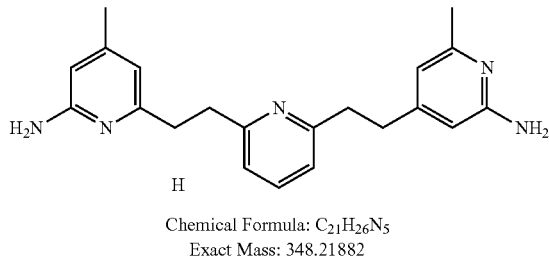

Chemical Formula: C$_{21}$H$_{26}$N$_5$
Exact Mass: 348.21882

4-(2-(6-(2-(6-Amino-4-methylpyridin-2-yl)ethyl)pyridin-2-yl)ethyl)-6-methylpyridin-2-amine (3m). Inhibitor 3m was synthesized using general method B (90%): $^1$H NMR (500 MHz, CDCl$_3$) δ 2.17 (s, 3H), 2.34 (s, 3H), 2.89-2.92 (m, 2H), 2.99-3.06 (m, 4H), 3.13-3.17 (m, 2H), 4.40 (br s, 2H), 4.43 (br s, 2H), 6.10-6.18 (m, 2H), 6.37-6.40 (m, 2H), 6.87-6.90 (dd, J=8.0, 8.0 Hz, 1H), 6.95-6.98 (dd, J=8.0, 8.0 Hz, 1H), 7.42-7.46 (m, 1H); $^{13}$C NMR (125 MHz, CD$_3$OD) δ 19.9, 22.2, 35.3, 37.5, 37.6, 37.9, 105.7, 106.8, 112.9, 113.4, 120.8, 120.9, 121.0, 137.46, 137.55, 150.0, 153.3, 155.3, 158.0, 159.3, 159.5, 160.3, 160.4, 160.8; LC-TOF (M+H$^+$) calcd for C$_{21}$H$_{26}$N$_5$ 348.21882, found 348.21880.

Example 31

Dimethyl 5-(2,5-dimethyl-1H-pyrrol-1-yl)isophthalate (9). To a solution of dimethyl 5-aminoisophthalate (8, 10.5 g, 50 mmol) in toluene (50 mL) was added acetonylacetone (6.18 mL, 52.5 mmol) and p-TsOH (95 mg, 0.5 mmol). The reaction mixture was heated in a Dean-Stark apparatus under reflux for 12 h. After cooling to room temperature, the mixture was concentrated with a rotary evaporator, and the resulting brown oil was purified by flash column chromatography (EtOAc/hexanes, 1:19-1:9) to give 9 (13.2 g, 46 mmol, 92%) as a white solid: $^1$H NMR (500 MHz, CDCl$_3$) δ2.05 (s, 6H), 3.99 (s, 6H), 5.95 (s, 2H), 8.11 (s, 2H), 8.74 (s, 1H); $^{13}$C NMR (125 MHz, CDCl$_3$) δ13.3, 52.9, 106.8, 128.9, 130.0, 132.0, 133.6, 139.9, 165.7; LC-MS (M+H$^+$) calcd for C$_{16}$H$_{18}$NO$_4$ 288, found 288.

Example 32

(5-(2,5-Dimethyl-1H-pyrrol-1-yl)-1,3-phenylene) dimethanol (10). To a solution of 9 (2.87 g, 10 mmol) in THF (60 mL) at −78° C. was added Dibal-H (1 M solution in toluene, 60 mL, 60 mmol) drop wise. The reaction mixture was slowly warmed to room temperature over a period of 6 h, and then quenched by sodium potassium tartrate (1 M, 40 mL). The THF was removed by rotary evaporation, and the resulting aqueous solution was extracted by ether (3×100 mL). The combined organic layers were dried over Na$_2$SO$_4$ and concentrated. The crude product was purified by flash column chromatography (EtOAc/hexanes, 2:1-4:1) to yield 10 (2.24 g, 97%) as a white solid (Caution: the product is not stable as solution forms, while stable in solid form for weeks at room temperature): $^1$H NMR (500 MHz, CDCl$_3$) δ 2.01 (s, 6H), 2.45 (s, 2H), 4.69-4.70 (d, J=5.5 Hz, 4H), 5.89 (s, 2H), 7.10 (s, 2H), 7.39 (s, 1H); $^{13}$C NMR (125 MHz, CDCl$_3$) δ13.1, 64.5, 105.8, 124.3, 125.6, 128.7, 139.3, 142.4; LC-MS (M+H$^+$) calcd for C$_{14}$H$_{18}$NO$_2$ 232, found 232.

Example 33

1-(3,5-Bis(bromomethyl)phenyl)-2,5-dimethyl-1H-pyrrole (5g). To a solution of 10 (500 mg, 2.35 mmol) in DCM (15 mL) at 0° C. was added Ph$_3$P (1.29 g, 4.93 mmol), followed by CBr$_4$ (1.62 g, 4.93 mmol). The reaction mixture was allowed to stir at room temperature for 1 h. The solvent was removed by rotary evaporation, and the resulting material was purified by flash column chromatography (EtOAc/hexanes, 1:18-1:9) to yield 5 g (655 mg, 79%) as a white solid (Caution: for long term storage, the product should be refrigerated at <20° C.): $^1$H NMR (500 MHz, CDCl$_3$) δ 2.05 (s, 6H), 4.49 (s, 4H), 5.90 (s, 2H), 7.19-7.20 (d, J=1.5 Hz, 2H), 7.43 (s, 1H); $^{13}$C NMR (125 MHz, CDCl$_3$) δ13.1, 32.0, 106.2, 128.4, 128.56, 128.61, 139.4, 139.7; LC-MS (M+H$^+$) calcd for C$_{14}$H$_{16}$Br$_2$N 356. found 356.

Example 34

16,6'-(2,2'-(5-(2,5-Dimethyl-1H-pyrrol-1-yl)-1,3-phenylene)bis(ethane-2,1-diyl)bis(2-(2,5-dimethyl-1H-pyrrol-1-yl)-4-methylpyridine) (6n). Compound 6n was synthesized starting with 7 and 5g using general method A (55%) 1H NMR (500 MHz, CDCl$_3$) δ1.94 (s, 6H), 2.11 (s, 12H), 2.35 (s, 6H), 3.07 (s, 8H), 5.85 (s, 2H), 5.88 (s, 4H), 6.81-6.82 (d, J=1.5 Hz, 2H), 6.85 (s, 2H), 6.87 (s, 2H), 7.06 (s, 1H); $^{13}$C NMR (125 MHz, CDCl$_3$) δ 13.0, 13.3, 21.0, 35.3, 39.4, 105.5, 106.6, 106.7, 120.1, 122.6, 125.7, 128.0, 128.4, 128.5, 138.9, 142.5, 149.4, 151.7, 160.5; LC-MS (M+H$^+$) calcd for C$_{40}$H$_{46}$N$_5$ 596, found 596.

Example 35

6,6'-(2,2'-(5-Amino-1,3-phenylene)bis(ethane-2,1-diyl)) bis(4-methylpyridin-2-amine) (3n). Inhibitor 3n was synthesized using general method B (85%): $^1$H NMR (500 MHz, CDCl$_3$) δ 2.20 (s, 6H), 2.83-2.84 (t, J=2.5 Hz, 8H), 3.49 (s, 2H), 4.49 (br s, 4H), 6.19 (s, 2H), 6.35 (s, 2H), 6.43 (s, 2H), 6.52 (s, 1H); $^{13}$C NMR (125 MHz, CDCl$_3$) δ21.3, 36.3, 39.9, 106.8, 113.2, 114.6, 119.5, 143.3, 146.6, 149.7, 158.2, 159.5; LC-TOF-MS (M+H$^+$) calcd for C$_{22}$H$_{28}$N$_5$ 362.23447, found 362.23399.

Figure 5:
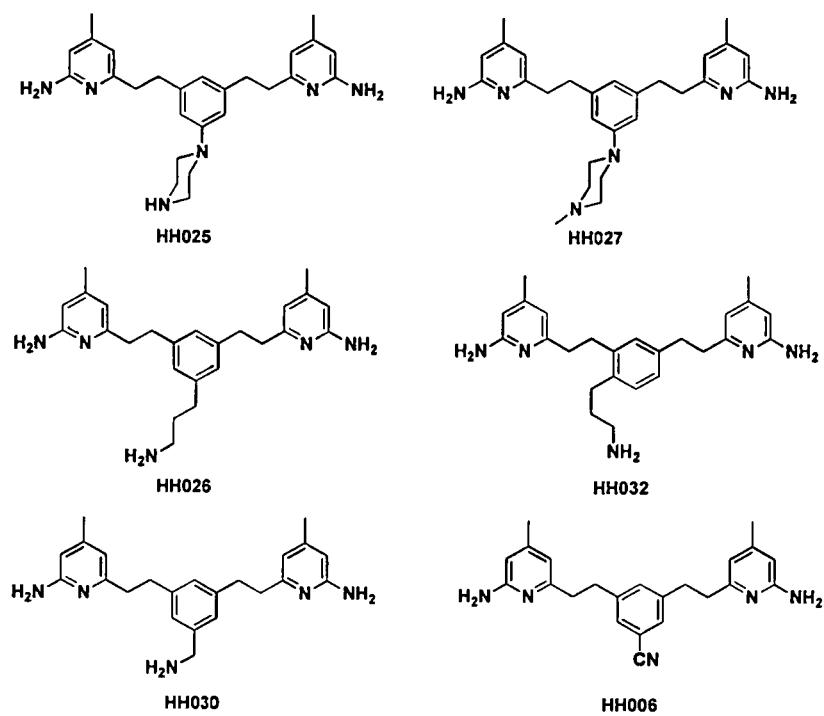
FIG. 5. Structures of various compounds of this invention, in accordance with certain non-limiting embodiments thereof.

With reference to Schemes 8-9 and FIG. 5, the corresponding target compounds are characterized, as provided in examples 36-41.

Example 36

6,6'-((5-(Piperazin-1-yl)-1,3-phenylene)bis(ethane-2,1-diyl)bis(4-methylpyridin-2-amine) (HH025): $^1$H NMR (500 MHz, D$_2$O): δ 6.64 (d, J=1.5 Hz, 2H), 6.56 (s, 1H), 6.46 (s, 2H), 6.23 (d, J=1.5 Hz, 2H), 3.29-3.25 (m, 8H), 2.82-2.81 (m, 8H), 2.09 (s, 6H). $^{13}$C NMR (125 MHz, D$_2$O): δ 157.75, 153.44, 148.52, 147.93, 141.52, 123.77, 116.34, 114.46, 109.38, 47.47, 42.69, 33.84, 29.49, 20.96.

Example 37

6,6'-((5-(4-Methylpiperazin-1-yl-1,3-phenylene)bis (ethane-2,1-diyl)bis(4-methylpyridin-2-amine) (HH027): $^1$H NMR (500 MHz, CDCl$_3$): δ 6.63 (s, 3H), 6.348 (d, J=1.5 Hz, 2H), 6.20 (s, 2H), 3.19 (t, J=5.0 Hz, 4H), 2.95-2.80 (m, 8H), 2.64-2.55 (m, 4H), 2.37 (s, 3H), 2.20 (s, 6H). $^{13}$C NMR (125

MHz, CDCl$_3$): δ 157.82, 148.81, 142.64, 141.84, 123.94, 120.45, 114.48, 114.09, 106.69, 55.15, 49.14, 46.07, 39.70, 36.44, 21.08.

Example 38

6,6'-((5-(3-aminopropyl)-1,3-phenylene)bis(ethane-2,1-diyl)bis(4-methylpyridin-2-amine) (HH026): $^1$H NMR (500 MHz, D$_2$O): δ 6.77 (d, J=1.5 Hz, 2H), 6.67 (t, J=1.5 Hz, 1H), 6.45 (s, 2H), 6.23 (d, J=1.5 Hz, 2H), 2.79 (s, 8H), 2.76-2.70 (m, 2H), 2.48-2.44 (m, 2H), 2.08 (s, 6H), 1.75-1.69 (m, 2H). $^{13}$C NMR (125 MHz, D$_2$O): δ 162.68, 157.75, 153.40, 148.08, 141.36, 140.23, 126.67, 114.40, 109.35, 38.95, 33.71, 33.60, 31.56, 29.44, 20.96.

Example 39

6,6'-((4-(3-aminopropyl)-1,3-phenylene)bis(ethane-2,1-diyl)bis(4-methylpyridin-2-amine) (HH032): $^1$H NMR (500 MHz, MeOD): δ 6.97-6.95 (m, 1H), 6.90-6.87 (m, 2H), 6.20-6.18 (m, 4H), 2.94-2.84 (m, 2H), 2.82-2.75 (m, 4H), 2.68-2.61 (m, 4H), 2.60-2.55 (m, 4H), 2.07 (s, 6H), 1.26-1.23 (m, 2H). $^{13}$C NMR (125 MHz, MeOD): δ160.33, 160.31, 160.12, 158.51, 152.01, 151.95, 151.93, 140.29, 137.19, 130.88, 130.21, 127.64, 127.62, 114.72, 114.62, 108.26, 39.95, 39.85, 36.70, 35.30, 30.35, 29.99, 23.89, 21.16, 21.13.

Example 40

6,6'-((5-(aminomethyl)-1,3-phenylene)bis(ethane-2,1-diyl))bis(4-methylpyridin-2-amine) (HH030): $^1$H NMR (500 MHz, MeOD): δ 7.06-6.96 (m, 3H), 6.34-6.21 (m, 4H), 2.92-2.88 (m, 4H), 2.85-2.73 (m, 6H), 2.17 (s, 6H). $^{13}$C NMR (125 MHz, MeOD): δ161.51, 160.68, 151.03, 129.67, 129.61, 126.26, 119.69, 114.67, 107.90, 40.66, 37.29, 24.25, 21.05.

Example 41

3,5-bis(2-(6-amino-4-methylpyridin-2-yl)ethyl)benzonitrile (HH006): $^1$H NMR (500 MHz, CDCl$_3$): δ 7.28 (d, J=1.5 Hz, 2H), 7.27-7.26 (m, 1H), 6.25 (s, 2H), 6.18 (s, 2H), 3.00-2.91 (m, 4H), 2.86-2.77 (m, 4H), 2.17 (s, 6H). $^{13}$C NMR (125 MHz, CDCl$_3$): δ 158.23, 158.19, 149.51, 143.10, 133.66, 129.69, 119.33, 114.44, 111.92, 106.86, 39.16, 35.40, 21.00.

Example 42

Enzyme Assays. IC$_{50}$ values for compounds 3a-m (Schemes 1-7) and the compounds of Schemes 8-9 were measured for three different isoforms of NOS including rat nNOS, bovine eNOS and murine macrophage iNOS using L-arginine as a substrate. The four enzyme isoforms were recombinant enzymes overexpressed (in *E. coli*) and isolated as reported. (See, Zhang, L.; Dawson, V. L.; Dawson, T. M. *Pharmacol. Ther.* 2006, 109, 33-41.) These enzymes are known to have very high sequence identity. The formation of nitric oxide was measured using a well-known hemoglobin capture assay, as described previously in the literature. All NOS isozymes were assayed at room temperature in a 100 mM hepes buffer (pH 7.4) containing 10 μM L-arginine, 1.6 mM CaCl$_2$, 11.6 μg/mL calmodulin, 100 μM DTT, 100 μM NADPH, 6.5 μM H$_4$B, and 3.0 mM oxyhemoglobin (for iNOS assays, no additional Ca$^{2+}$ and calmodulin) were included. The assay was initiated by the addition of enzyme, and the initial rates of the enzymatic reactions were determined on a UV-vis spectrometer by monitoring the formation of NO-hemoglobin complex at 401 nm from 0 to 60 s after mixing. The corresponding K$_i$ values of inhibitors were calculated from the IC$_{50}$ values using equation 1 with known K$_m$ values (human nNOS, 1.6 μM; rat nNOS, 1.3 μM; iNOS, 8.3 μM; eNOS, 1.7 μM).

$$K_i = IC_{50}/(1+[S]/K_m) \quad (1)$$

We claim:

1. A nitric oxide synthase inhibitor compound of a formula

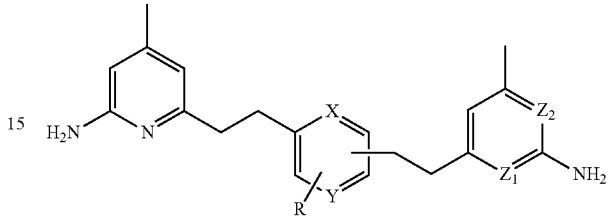

wherein R is selected from H, halogen, amino, nitrile, alkyl, haloalkyl, aminoalkyl, cyanoalkyl, cycloalkyl and azacycloalkyl moieties; X and Y are independently selected from CR' and N, where R' is selected from H and R, and providing at least one of X and Y is CR; and Z$_1$ and Z$_2$ are independently selected from CH and N, providing one of Z$_1$ and Z$_2$ is N; and a salt thereof.

2. The compound of claim 1 wherein each of X and Y is CR'.

3. The compound of claim 2 wherein X is CH and Y is CR, and each said pendent aminopyridine moiety has a relationship to CR selected from ortho and meta-relationships.

4. The compound of claim 3 wherein each said relationship is meta.

5. The compound of claim 4 wherein R is selected from nitrile and aminoalkyl moieties.

6. The compound of claim 1 wherein Y is N, and said pendent aminopyridine moieties have a meta-relationship one to another.

7. The compound of claim 6 wherein X is CH, and R is selected from H, nitrile and aminoalkyl moieties.

8. The compound of claim 6 wherein X is CR' and R' is selected from H, nitrile and aminoalkyl moieties.

9. The compound of claim 1 wherein said compound is an ammonium salt.

10. The compound of claim 9 wherein said salt has a counter ion that is a conjugate of a protic acid.

11. A compound of a formula

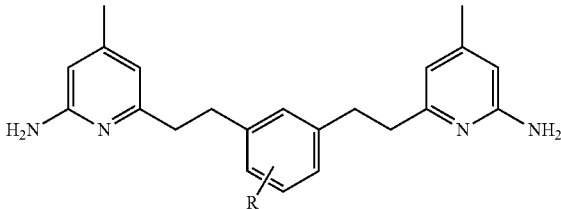

wherein R is selected from H, halogen, amino, nitrile, alkyl, haloalkyl, aminoalkyl, cyanoalkyl, cycloalkyl and azacycloalkyl moieties; and a salt thereof.

12. The compound of claim 11 wherein R is selected from nitrile and aminoalkyl moieties.

13. The compound of claim 12 wherein R is a nitrile moiety, with a meta-relationship to each said pendent aminopyridine moiety.

14. The compound of claim 11 where said compound is an ammonium salt.

15. The compound of claim 14 wherein said salt has a counter ion that is a conjugate of a protic acid.

16. A method of inhibiting a nitric oxide synthase comprising contacting a nitric oxide synthase with an effective amount of a compound of a formula

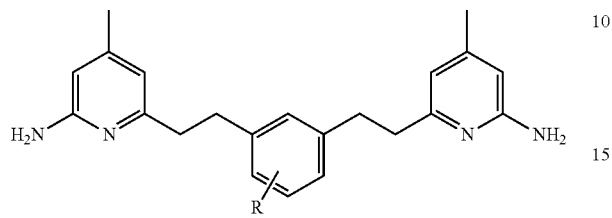

or a salt thereof.

17. The method of claim 16 wherein R is selected from nitrile and aminoalkyl moieties.

18. The method of claim 16 wherein R is nitrile.

19. The method of claim 18 wherein R has a meta-relationship to each said pendent aminopyridine moiety.

20. The method of claim 17 selective for inhibition of neuronal nitric oxide synthase.

* * * * *